United States Patent
Leonardi et al.

(10) Patent No.: US 6,440,963 B1
(45) Date of Patent: Aug. 27, 2002

(54) USE OF SELECTIVE COX-2 INHIBITORS FOR THE TREATMENT OF URINARY INCONTINENCE

(75) Inventors: Amedeo Leonardi, Milan; Rodolfo Testa, Vignate; Luciano Guarneri, Garbagnate, all of (IT)

(73) Assignee: Recordati S.A., Chemical and Pharmaceutical Company, Chiasso (CH)

(*) Notice: Subject to any disclaimer, the term of this patent is extended or adjusted under 35 U.S.C. 154(b) by 0 days.

(21) Appl. No.: 09/969,538

(22) Filed: Oct. 1, 2001

(30) Foreign Application Priority Data

Apr. 5, 2001 (IT) .......................................... MI01A0733

(51) Int. Cl.$^7$ ........................ A61K 31/54; A61K 31/50; A61K 31/425; A61K 31/415; A61K 31/16
(52) U.S. Cl. .................... 514/226.5; 514/247; 514/368; 514/406; 514/407; 514/600
(58) Field of Search .............................. 514/226.5, 247, 514/368, 406, 407, 600

(56) References Cited

U.S. PATENT DOCUMENTS

| | | |
|---|---|---|
| 4,166,452 A | 9/1979 | Generales, Jr. ............. 128/741 |
| 4,233,299 A | 11/1980 | Trummlitz et al. ......... 424/246 |
| 4,256,108 A | 3/1981 | Theeuwes .................... 128/260 |
| 4,265,874 A | 5/1981 | Bonsen et al. ................ 424/15 |
| 4,321,118 A | 3/1982 | Felder et al. .......... 204/159.18 |
| 4,375,479 A | 3/1983 | Schroeder et al. ........... 424/321 |
| 5,474,994 A | 12/1995 | Leonardi et al. ............. 514/218 |
| 5,552,422 A | 9/1996 | Gauthier et al. ............. 514/368 |
| 5,633,272 A | 5/1997 | Talley et al. ................. 514/378 |

FOREIGN PATENT DOCUMENTS

| | | | |
|---|---|---|---|
| WO | WO 94/13635 | 6/1994 | ......... C07C/323/49 |
| WO | WO 95/15316 | 6/1995 | ......... C07D/231/12 |
| WO | WO 96/09304 | 3/1996 | ....... C07D/491/048 |
| WO | WO 97/36863 | 10/1997 | ......... C07C/323/22 |
| WO | WO 97/38986 | 10/1997 | ......... C07D/261/08 |
| WO | WO 98/09948 | 3/1998 | ......... C07D/213/00 |
| WO | WO 99/10331 | 3/1999 | ......... C07D/237/14 |

OTHER PUBLICATIONS

Friedman, M., et al., "Octaarylporphyrins" *J. Org. Chem.,* 30:859–863 (1965).

Friesen, R. W., et al., "2–Pyridinyl–3–(4–Methylsulfonyl) Phenylpyridines: Selective and Orally Active Cyclooxygenase–2 Inhibitors", *Bioorganic & Medicinal Chemistry Letters,* 8:2777–2782 (1998).

Ghoneim, M.A., et al., "The Influence of Vesical Distension on the Urethral Resistance to Flow: A Possible Role for Prostaglandins?", *Journal of Urology,* 116:739–743 (1976).

Gierse, J.K., et al., "Expression and Selective Inhibition of the Constitutive and Inducible Forms of Human Cyclo–Oxygenase", *Biochem J.,* 305:479–484 (1995).

Girard, Y., et al., "Synthesis, Chemistry, and Photochemical Substitutions of 6,11–Dihydro–5H–pyrrolo[2,1–b][3] benzazpine–11–ones", *J. Organic Chemistry,* 48:3220–3234 (1983).

Gotoh, M., et al., "The Mode of Action of Prostaglandin $E_2$, $F_{2a}$ and Prostacyclin on Vesicourethral Smooth Muscle", *Journal of Urology,* 135:431–437 (1986).

Guarneri, L., et al., "Effects of Drugs Used in the Therapy of Detrusor Hyperactivity on the Volume–Induced Contractions of the Rat Urinary Bladder", *Pharmacological Research,* 27:173–187 (1993).

Huang, H.C., et al., "A Novel One–Pot Conversion of Methyl Sulfones to Sulfonamides", *Tetrahedron Letters,* 35:7021–7204 (1994).

Husted, S., et al., "Role of Prostaglandins in the Responses of Rabbit Detrusor to Non–Cholinergic, Non–Adrenergic Nerve Stimulation and to ATP", *Arch. Int. Pharmacodyn,* 246:84–97 (1980).

Jackson, S., et al., "The Bristol Female Lower Urinary Tract Symptoms Questionnaire: Development and Psychometric Testing", *British Journal of Urology,* 77:805–812 (1996).

Khanna, I.K., et al., "Selective Cyclooxygenase–2 Inhibitors: Heteroaryl Modified 1,2–Diarylimidazoles Are Potent, Orally Active Antiinflammatory Agents", *J. Med. Chem.,* 43:3168–3185 (2000).

Kharash, N., et al., "Derivatives of Sulfenic Acids. V. 1–Fluorenone Sulfur Compounds", *Journal American Chemical Society,* 73:3240–3244 (1951).

Lau, C.K., et al., "Reductive Deoxygenation of Aryl Aldehydes and Ketones and Benzylic, Allylic, and Tertiary Alcohols by $ZnI_2$–$NaCNBH_3$", *J. Org. Chem,* 51:3038–3043 (1986).

Lecci, A., et al., "Pharmacological Evaluation of the Role of Cycolooxygenase Isoenzymes on the Micturition Reflex Following Experimental Cystitis in Rats", *British Journal of Pharmacology,* 130:331–338 (2000).

Maggi, C.A., et al., "The Contribution of Capsaicin–Sensitive Innervation to Activation of the Spinal Vesico–Vesical Reflex in Rats:Relationship Between Substance P Levels in the Urinary Bladder and the Sensory–Efferent Function of Capsaicin–Sensitive Sensory Neurons", *Brain Research,* 415:1–13 (1987).

Maggi, C.A., et al., "The Capsaicin–Sensitive Innervation of the Rat Urinary Bladder: Further Studies on Mechanisms Regulating Micturition Threshold", *Journal of Urology,* 136:696–700 (1986).

(List continued on next page.)

*Primary Examiner*—Raymond Henley, III
(74) *Attorney, Agent, or Firm*—Darby & Darby

(57) ABSTRACT

The treatment of neuromuscular dysfunction of the lower urinary tract by compounds which selectively inhibit the COX-2 isozyme is described. The compounds concerned inhibit the COX-2 isozyme with a potency at least 10-fold, and preferably at least 100-fold, greater than their potency on the COX-1 isozyme.

83 Claims, No Drawings

OTHER PUBLICATIONS

Maggi, C.A., et al., "Evidence for the Involvement of Arachidonic Acid Metabolites in Spontaneous and Drug-Induced Contractions of Rat Urinary Bladder", *Journal of Pharmacology and Experimental Therapeutics*, 230:500–513 (1984).

Pairet, M., et al., "Tests for Cyclooxygenase–1 and –2 Inhibition" in *Clinical Significance and Potential of Selective COX–2 Inhibitors*, (J. Van and R. Bottings eds.), pp. 19–30, William Harvey Press (1998).

Palea, S., et al., "Pharmacological Characterization of Thromboxane and Prostanoid Receptors in Human Isolated Urinary Bladder", *British Journal of Pharmacology*, 124:865–872 (1998).

Penning, T.D., et al., "Synthesis and Biological Evaluation of the 1,5–Diarylpyrazole Class of Cyclooxygenase–2 Inhibitors: Identification of 4-[5-(4-Methylphenyl)-3-(trifluoromethyl)-1H-pyrazol-1-yl] benzenesulfonamide (SC–58635, Celecoxib)", *J. Med. Chem.*, 40:1347–1365 (1997).

Reid, J.C., et al., "Some New β–Diketones Containing the Trifluoromethyl Group", *Journal American Chemical Society*, 72:2948–2952 (1950).

Riendeau, D., et al., "Biochemical and Pharmacological Profile of a Tetrasubstituted Furanone as a Highly Selective COX–2 Inhibitor", *British Journal of Pharmacology*, 121:105–117 (1997).

Rutsch, W., et al., "New Photoinitiators for Pigmented Systems", *Org. Coat.*, 8:175–195 (1986).

Schulze, von Bärbel, et al., "Zur Oxidation von 1,2–Thiazolen: Ein einfacher Zugang zu 1,2–Thiazol–3(2H)–on–1,1–dioziden", *Helvetica Chimica Acta*, 74:1059 (1991) Abstract In English.

Tallarida, R.J., et al., *"Manual of Pharmacologic Calculations with Computer Programs"*, Second Edition, pp. 10–13, Springer–Verlag (1987).

Weissenfels, et al., "Zur Kondensation von β–Chlorvinylcarbonylverbindungen mit α–Mercaptocarbonsäuren", *Z. Chem.*, 13:57–58 (1973).

Weissenfels, et al., "β–Chlorvinylaidehyde nach dem Vilsmeier–Prinzip", *Z. Chem.*, 6:471–472 (1966).

Yamamoto, T., et al., "Analysis of the Effects of Cyclooxygenase (COX)–1 and COX–2 in Spinal Nociceptive Transmission Using Indomethacin, a Non–Selective COX Inhibitor, and NS–398, a COX–2 Selective Inhibitor", *Brian Research*, 739:104–110 (1996).

Yasojima, K., et al., "Distribution of Cyclooxygenase–1 and Cyclooxygenase–2 mRNAs and Proteins in Human Brain and Peripheral Organs", *Brian Research*, 830:226–236 (1999).

Aliev et al. Sulfur Lett. 12:123–132 (1991).

Dimroth et al. Ann. 639:102 (1961).

Andersson, K.E., et al., "Effects of Prostaglandins on the Isolated Human Bladder and Urethra", *Acta Physiol. Scand.* 100:165–171 (1977).

Andersson, K.E., "Current Concepts in the Treatment of Disorders of Micturition", *Drugs*, 35;477–494 (1988).

Aslam, M., et al., "Anhydrous Hydrogen Fluoride Catalyzed Friedel–Crafts Reactions of Thioaromatic Compounds", *J. Organic Chemistry*, 56:5955–5958 (1991).

Barry, M.J., "The American Urological Association Symptom Index for Benign Prostatic Hyperplasia", *Journal of Urology*, 148:1549–1557 (1992).

Basha, A., et al., "A Mild, General Method for Conversion of Esters of Amides", *Tetrahedron Letters*, 48:4171–4174 (1977).

Borda, E., et al., "Relationships Between Prostaglandins and Estrogens on the Motility of Isolated Rings from the Rat Urinary Bladder", *Journal of Urology*, 129:1250–1253 (1983).

Breder, C.D., et al., "Characterization of Inducible Cyclooxygenase in Rat Brain", *Journal of Comparative Neurology*, 355:296–315 (1995).

Brederick, H., et al., "Imidazolsynthesen mit Formamid (Formamid–Reaktionen, I. Mitteil), *Chem. Ber.*, 86:88–96 (1953).

Dimroth, K., et al., "Über ungesättigte heterocyclische Siebenringsysteme mit aromatischen Eigenschaften. I. Mitteil.: Derivate des Aza–tropilidens", *Ber.*, 56:2602–2607 (1956).

Downie, J.W., et al., "Mechanical Trauma to Bladder Epithelium Liberates Prostanoids which Modulate Neurotransmission in Rabbit Detrusor Muscle", *Journal of Pharmacology and Experimental Therapeutics*, 230:445–449 (1984).

Dray, A., "The Rat Urinary Bladder: A Novel Preparation for the Investigation of Central Opioid Activity In Vivo", *Journal of Pharmacological Methods*, 13:157–165 (1985).

Ehrich, E.W., et al., "Characterization of Rofecoxib as a Cyclooxygenase–2 Isoform Inhibitor and Demonstration of Analgesia in the Dental Pain Model", *Clinical Pharmacology & Therapeutics*, 65:336–347 (1999).

USE OF SELECTIVE COX-2 INHIBITORS FOR THE TREATMENT OF URINARY INCONTINENCE

The present application claims priority under 35 U.S.C.§ 119 (a)–(d) of Italian patent application no. MI 2001 A 000733, which is hereby incorporated herein by reference in its entirety.

FIELD OF THE INVENTION

The invention relates to compositions and methods for treating neuromuscular dysfunction of the lower urinary tract in mammals, including humans, using selective inhibitors of the cyclooxygenase-2 isozyme (COX-2).

BACKGROUND OF THE INVENTION

In mammals, micturition is a complex process that requires the integrated actions of the bladder, its internal and external sphincters, and the musculature of the pelvic floor. Neurological control over these muscles occurs at three levels—in the bladder wall or sphincters, in the autonomic ganglia of the spinal cord, and in the central nervous system in the pontine micturition center of the brainstem (pons), under the control of the cerebral cortex.

Micturition results from contraction of the bladder detrusor muscle, which consists of interlacing smooth muscle fibers that are under parasympathetic autonomic control from the sacral spinal cord. A simple voiding reflex is formed by sensory nerves for pain, temperature, and distension that run from the bladder to the sacral cord. However, sensory tracts from the bladder also reach the pontine micturition center, resulting in the generation of nerve impulses that normally act at the spinal cord to suppress the sacral spinal reflex arc controlling bladder emptying. As a result, normal micturition is initiated by voluntary suppression of the cortical inhibition of the reflex arc and by relaxation of the muscles of the pelvic floor and the external sphincter. These events are followed by contraction of the detrusor muscle and voiding.

Functional abnormalities of the lower urinary tract, e.g., dysuria, incontinence, and enuresis, are common in the general population. Dysuria includes urinary frequency, nocturia, and urgency, and may be caused by cystitis, prostatitis or benign prostatic hypertrophy, which affects about 70% of elderly males, or by neurological disorders. Incontinence syndromes include stress incontinence, urgency incontinence, and overflow incontinence. Enuresis refers to the involuntary passage of urine at night or during sleep.

Prior to the present invention, treatment of neuromuscular disorders of the lower urinary tract has involved administration of compounds that act directly on the bladder muscles, such as flavoxate, a spasmolytic drug that is also active on the pontine micturition center, or anticholinergic compounds such as oxybutynin. The use of $\alpha$1-adrenergic receptor antagonists for the treatment of benign prostatic hypertrophy is also common. However, treatments that involve direct inhibition of the pelvic musculature or detrusor muscle may have undesirable side effects, such as incomplete voiding, accommodation reflex paralysis, tachycardia and dry mouth. Thus, it would be preferable to treat neuromuscular disorders of the lower urinary tract with compounds that act via the peripheral or central nervous system, to affect, for example, the sacral spinal reflex arc and/or the inhibitory impulses of the pontine micturition center in a manner that restores normal functioning of the micturition mechanism.

Available evidence indicates that arachidonic acid metabolites produced via the cyclooxygenase (COX) pathway are involved in the physiological regulation of the micturition reflex. Prostaglandin $E_1$ ($PGE_1$), $PGE_2$, $PGD_2$, $PGF_{2\alpha}$ as well as tromboxane $A_2$ ($TXA_2$) have been shown to induce contractile activity of animal and human bladder detrusor, in vitro (Andersson et al., Acta Physiol. Scand. 100:165–171, 1977; Borda et al., J. Urol. 129:1250–1253, 1983; Maggi et al., J. Pharmacol. Exp. Ther. 230:500–513, 1984; Gotoh et al., J. Urol. 135:431–437, 1986; and Palea et al., Br. J. Pharmacol. 124:865–872, 1998). $PGE_2$ and $PGF_{2\alpha}$ also play a role in modulating cholinergic and purinergic contractions generated by electrical stimulation, as demonstrated in isolated rabbit urinary bladder (Downie et al., J. Pharmacol. Exp. Ther. 230:445–449, 1984 and Husted et al, Arch. Intl. Pharmacodyn. 246:84–97, 1980). Furthermore, distension of the bladder wall leads to local production of endogenous prostanoids that modulate the afferent branch of the micturition reflex by lowering the threshold for eliciting voiding contractions (Ghoneim et al., J. Urol. 116:739–743, 1976), thus representing the link between stretching of the detrusor muscle due to bladder filling and activation of capsaicin-sensitive afferents.

Accordingly, indomethacin and flurbiprofen, well known inhibitors of cyclooxygenase, showed favorable effects in double-blind controlled studies in patients with detrusor instability, although they did not completely abolish detrusor overactivity and showed a high incidence of gastrointestinal side effects (Andersson, Drugs 35:477–494, 1988).

Prostaglandins are produced from free arachidonic acid through the catalytic activity of two COX enzymes. COX-1 is considered the constitutive isoform, being expressed in almost all tissues, whereas COX-2 is considered inducible, since its expression can be triggered typically by inflammatory insults. Several groups, however, have reported constitutive expression of COX-2 in different tissues, including the central nervous system (Yasojima et al., Brain Res. 830:226–236, 1999).

In the brainstem, COX-2-containing neurons were observed in the dorsal raphe nucleus, the nucleus of the brachium of the inferior colliculus, and in the region of the subcoeruleus, suggesting that COX-2 may be involved in the processing and integration of visceral sensory input and in the modulation of autonomic responses (Breder et al., J. Comp. Neurol. 355:296–315, 1995). Furthermore, it has been demonstrated (Yamamoto et al., Brain Res. 739:104–110, 1996) that COX-2 is constitutively expressed in the spinal cord, where it plays an important role in the spinal nociceptive information transmission.

Previous attempts did not establish a role for COX-2 specific antagonists in the treatment of non-inflammatory based neuromuscular dysfunction of the lower urinary tract. Lecci et al. (Br. J. Pharm. 130:331–338, 2000) compared the effects of a non-selective COX-1/COX-2 inhibitor, dexketoprofen, and a COX-2 selective inhibitor, NS-398, on urodynamic function, in both inflammation-based and non-inflammation based rat models. Bladder contractions elicited by application of arachidonic acid onto the serosal surface of the urinary bladder were blocked by dexketoprofen, but not by NS-398. Furthermore, although both dexketoprofen and NS-398 normalized bladder reflexes following either surgery or experimentally-induced inflammation of the lower urinary tract, there was no enhanced effect evidenced by the COX-2-specific inhibitor.

Lecci et al., therefore, failed to show any effect of NS-398 in a non-inflammation-based model of bladder function. Nor did Lecci et al. demonstrate a selective effect of a COX-2 inhibitor in inflammation-based models of urodynamic function. Nor did Lecci et al. demonstrate that selective COX-2 inhibitors are more potent than non-selective COX-1/COX-2 inhibitors at inhibiting the central part of the micturition reflex. Given these results, Lecci et al. speculated that, under non-inflammatory conditions, only the blockade of both COX-1 and COX-2 leads to urodynamic changes.

PCT application WO 98/09948 measured the effect in vitro of the COX-2 specific inhibitor, nimesulide, on contractility of isolated rat bladder strips stimulated with 40 mM potassium. Nimesulide was ineffective at inhibiting contractility, in that a high concentration ($1 \times 10^{-4}$M) of nimesulide achieved only a 42% inhibition. The requirement for such a high concentration suggests that the observed effect was not to due neuronal control of micturition, but rather was due to local effect of nimesulide on the bladder dome tissue.

Thus, there remains a need in the art for potent COX-2 specific inhibitors that are effective in treating neuromuscular dysfunction of the lower urinary tract. In particular, there remains a need for COX-2 specific inhibitors that are effective in treating neuromuscular dysfunction by acting upon the micturition reflex.

We have tested selective and non-selective (e.g. indomethacin) COX-2 inhibitors for their activity on the lower urinary tract in the rat. Using an animal model that reflects the central mechanisms underlying bladder control to test the effects of specific and non-specific COX-2 inhibitors on bladder function, we have found, unexpectedly, that selective COX-2 inhibitors proved very potent in inhibiting frequency of bladder contraction.

Given these results, selective COX-2 inhibitors can be an effective means to treat urinary tract disorders.

SUMMARY OF THE INVENTION

The invention is based on the finding that selective COX-2 inhibitors are useful in the treatment of neuromuscular dysfunction of the lower urinary tract in mammals.

Thus, the invention provides methods for treating neuromuscular dysfunction of the lower urinary tract in mammals, including without limitation, dysuria, incontinence, and enuresis. The methods involve administering to affected mammals in need thereof effective amounts of compounds for treating the disorders with selective COX-2 inhibitors, preferably having the structures of the formulas I to VI below:

1) Compounds of General Formula I

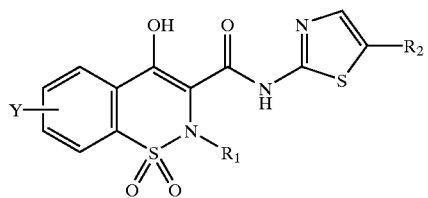

(I)

or a pharmacologically acceptable salt thereof wherein, independently:

$R_1$ represents a hydrogen atom or a methyl or ethyl group;
$R_2$ represents a methyl, ethyl or n-propyl group; and
Y represents a hydrogen, fluorine or chlorine atom or a methyl or methoxy group.

In a preferred embodiment, $R_1$ and $R_2$ both represent methyl groups and Y represents a hydrogen atom. This is the compound 1,1-dioxo-4-hydroxy-2-methyl-N-(5-methyl-2-thiazolyl)-2H-1,2-benzothiazine-3-carboxamide (Compound A).

2) Compounds of General Formula II:

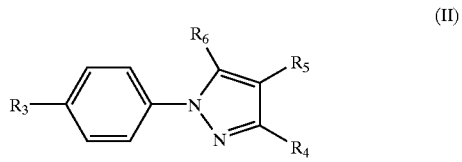

(II)

or a pharmacologically acceptable salt thereof wherein, independently:

$R_3$ represents $NHS(O)_2CH_3$, $S(O)_2CH_3$, $S(O)_2NH_2$, $S(O)(NH)NH_2$, or $S(O)_2NHC(O)(CH_2)_{1-3}CH_3$;

$R_4$ represents a halogen atom or a haloalkyl, cyano, nitro, aminocarbonyl, N-alkylaminocarbonyl, N,N-dialkylaminocarbonyl, cycloalkylaminocarbonyl, haloaralkyl, aminocarbonylhaloalkyl, alkylsulfonyl or N-alkylaminosulfonyl group;

$R_5$ represents a hydrogen or halogen atom or an alkyl, thio, alkylthio, haloalkyl, cyano, hydroxyalkyl, alkylsulfonyl or cycloalkyl group; and $R_6$ represents an aryl, cycloalkyl, cycloalkenyl or heterocyclic group and is optionally substituted with one or more radicals selected from the group consisting of halogen atom, alkylthio, alkyl, alkenyl, alkylsulfonyl, cyano, aminocarbonyl, haloalkyl, hydroxy, alkoxy, hydroxyalkyl, haloalkoxy, sulfamyl, amino, heterocyclic, cycloalkylalkyl and nitro groups; or $R_5$ and $R_6$ together with the pyrazole ring atoms to which they are attached form a 6- or 7-membered ring in which the ring atom next to that in the 4-position in the pyrazole ring is a sulfur atom, the 6- or 7-membered ring optionally being fused with a benzene ring which itself may be substituted with one or more halogen atoms and or $C_{1-4}$ alkyl groups.

The preferred group that $R_3$ represents is $S(O)_2NH_2$. The preferred haloalkyl that $R_4$ represents is trifluoromethyl. The preferred aryl group that $R_6$ represents is phenyl, optionally substituted with a radical selected from the group consisting of halogen atom, $C_{1-4}$-alkyl, $C_{2-4}$-alkenyl, $C_{1-4}$-haloalkyl, hydroxyl, $C_{1-4}$-alkoxy, hydroxyalkyl, haloalkoxy, and amino groups. All of the foregoing are independent preferences available in all combinations.

Preferred simultaneously are where $R_3$ is $S(O)_2NH_2$, $R_4$ is trifluoromethyl, $R_5$ is hydrogen and $R_6$ represents phenyl substituted with a methyl, ethyl, methoxy or ethoxy group.

When $R_5$ and $R_6$ are taken together as described above, they preferably form a group represented by the structure,

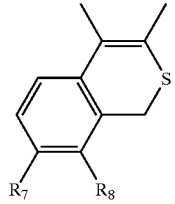

wherein $R_7$ represents a $C_{1-4}$ lower alkoxy group and $R_8$ represents a halogen atom. Most preferred is where $R_7$ represents methoxy and $R_8$ represents fluorine.

Synthesis of the compounds of formula II are described in WO 95/15316 and WO 96/09304. Additional chemistry relevant to synthesis of compounds of formula II may be found in Reid et al. (J. Amer. Chem. Soc. 72:2948–2952, 1950).

3) Compounds of General Formula III:

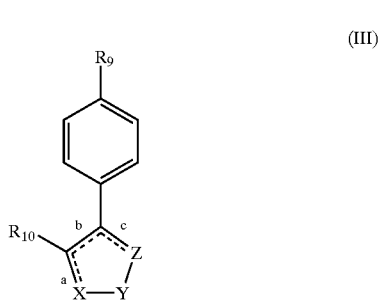

(III)

or a pharmaceutically acceptable salt thereof,
wherein
when side b is a double bond and sides a and c are single bonds X-Y-Z represents one of the groups
—CH$_2$CH$_2$CH$_2$—,
—C(O)CH$_2$CH$_2$—,
—CH$_2$CH$_2$C(O)—,
—CR$_{11}$(R'$_{11}$)—O—C(O)—,
—C(O)—O—CR$_{11}$(R'$_{11}$)—,
—CR$_{11}$(R'$_{11}$)—NR$_{12}$—C(O)—,
—N=CR$_{13}$—O—,
—O—CR$_{13}$=N—, or
—C(O)—NR$_{12}$—CR$_{11}$(R'$_{11}$)—;
or when sides a and c are double bonds and side b is a single bond X-Y-Z represents one of the groups
=CH—O—CH=,
=CH—CR$_{11}$(R'$_{11}$)—CH=,
=CH—NR$_{12}$—CH=,
=N—O—CR$_{11}$=,
=CH—O—N=, or
=N—O—N=;
where R$_9$ represents a NHS(O)$_2$CH$_3$, S(O)$_2$CH$_3$, S(O)$_2$NH$_2$, S(O)(NH)NH$_2$, or S(O)$_2$NHC(O)(CH$_2$)$_{1-3}$CH$_3$, group;
R$_{10}$ represents a C$_{1-6}$-alkyl or C$_{3-7}$-cycloalkyl group or an unsubstituted, mono-, di- or tri-substituted phenyl or naphthyl group, wherein each substituent of the phenyl or naphthyl group is selected from the group consisting of halogen atom, C$_{1-6}$-alkyl, C$_{1-6}$ alkoxy, cyano and trifluoromethyl groups;
R$_{11}$ and R'$_{11}$ are each independently selected from the group consisting of hydrogen atom and C$_{1-6}$-alkyl group;
R$_{12}$ is selected from the group consisting of hydrogen atom, trifluoromethyl, C$_{1-6}$-alkyl, hydroxy, and C$_{1-6}$-alkoxy group; and
R$_{13}$ is selected from the group consisting of hydrogen atom, trifluoromethyl and C$_{1-6}$-alkyl groups.

The following are independent preferences:
Preferred groups that R$_9$ represents are S(O)$_2$CH$_3$, S(O)$_2$NH$_2$ or S(O)$_2$NHC(O)(CH$_2$)$_{1-3}$CH$_3$.
The preferred groups that R$_{10}$ represents are mono-, di-, or tri-substituted phenyl groups. More preferred is where R$_{10}$ is a mono-, di-, or tri-fluorophenyl group.
Preferred groups that R$_{11}$ and R'$_{11}$ may represent independently are hydrogen or methyl.
Preferred groups that R$_{12}$ represents are hydrogen, trifluoromethyl, methyl, ethyl, hydroxy, methoxy, or ethoxy.

Preferred alkyl groups that R$_{13}$ represents are methyl or ethyl.

One preferred subgroup of compounds within the embodiment of formula III are compounds of formula IV(i)

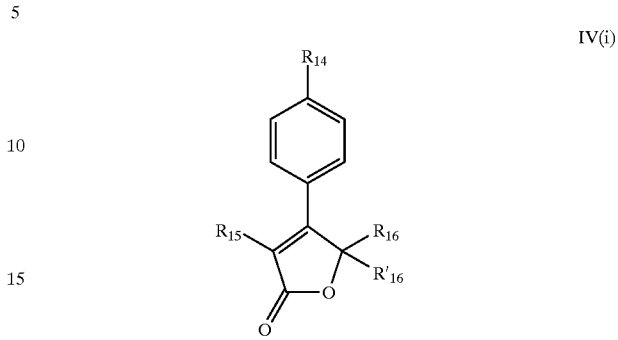

IV(i)

or a pharmaceutically acceptable salts thereof wherein:
R$_{14}$ represents a group of the formula S(O)$_2$CH$_3$ or S(O)$_2$NH$_2$;
R$_{15}$ represents a C$_{1-6}$-alkyl or C$_{3-7}$-cycloalkyl group or an unsubstituted, mono- or di-substituted phenyl group, wherein each substituent of the phenyl group is selected from the group consisting of halogen atom, C$_{1-6}$-alkyl, C$_{1-6}$-alkoxy, cyano, and trifluoromethyl groups; and
each of R$_{16}$ and R'$_{16}$ independently represents a hydrogen atom or a C$_{1-6}$-alkyl group.

Preferred alkyl groups that R$_{15}$ may represent are methyl or ethyl groups. Preferred phenyl groups that R$_{15}$ may represent are an unsubstituted phenyl group or a phenyl group substituted with 1 or 2 substituents selected from the group consisting of halogen atom, methyl, ethyl, methoxy, ethoxy, and trifluoromethyl groups. More preferred, R$_{15}$ may represent an unsubstituted phenyl group or a phenyl group substituted with 1 or 2 halogen atoms. Most preferably, R$_{15}$ may represent an unsubstituted phenyl group or a phenyl group substituted with 1 or 2 fluorine atoms.

Preferred alkyl groups that each of R$_{16}$ and R'$_{16}$ independently represent are methyl or ethyl groups. More preferred is where each of R$_{16}$ and R'$_{16}$ are hydrogen atoms.

Another preferred subgroup of compounds within the embodiment of formula III are compounds of formula IV(ii)

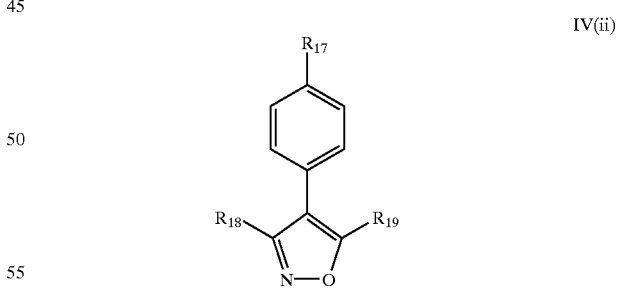

IV(ii)

or pharmaceutically acceptable salts thereof wherein:
R$_{17}$ represents NHS(O)$_2$CH$_3$, S(O)$_2$CH$_3$, S(O)$_2$NH$_2$, S(O)(NH)NH$_2$, or S(O)$_2$NHC(O)(CH$_2$)$_{1-3}$CH$_3$;
R$_{18}$ represents a C$_{1-6}$-alkyl, C$_{3-7}$-cycloalkyl group or an unsubstituted, mono- or di-substituted phenyl group, wherein each substituent substituent of the phenyl group is selected from the group consisting of halogen atom, C$_{1-6}$-alkyl, C$_{1-6}$-alkoxy, cyano, and trifluoromethyl groups; and
R$_{19}$ represents a hydrogen atom or a C$_{1-6}$-alkyl group.

Preferred groups that $R_{17}$ represents are $S(O)_2NH_2$ or $S(O)_2NHC(O)CH_2CH_3$.

Preferred alkyl groups that $R_{18}$ may represent are methyl or ethyl. Preferred phenyl groups that $R_{18}$ may represent are phenyl groups, optionally substituted with 1 or 2 substituents selected from the group consisting of halogen atom, methyl, ethyl, methoxy, ethoxy, and trifluoromethyl groups. More preferred, $R_{18}$ may represent a phenyl group, optionally substituted with 1 or 2 halogen atoms. Still more preferably, $R_{18}$ may represent a phenyl group, optionally substituted with 1 or 2 fluorine atoms. Most preferably, $R_{18}$ represents an unsubstituted phenyl group.

Preferred alkyl groups that each of $R_{19}$ represents are methyl or ethyl groups. Most preferably, $R_{19}$ is a methyl group.

A preferred embodiment is where, simultaneously, $R_{17}$ is $S(O)_2NH_2$, $R_{18}$ is an unsubstituted phenyl group and $R_{19}$ is a methyl group.

Another preferred embodiment is where, simultaneously, $R_{17}$ is $S(O)_2NHC(O)CH_2CH_3$, $R_{18}$ is an unsubstituted phenyl group and $R_{19}$ is a methyl group.

The synthesis of compounds of formula III, IV(i) and IV(ii) are described in U.S. Pat. Nos. 5,474,995 and 5,633,272 and in international publication WO 97/38986, respectively. Other general methods used in synthesizing compounds of formula III, IV(i) and IV(ii) can be found in Weissenfels (Z. Chem. 6:471, 1966); Weissenfels (Z. Chem. 13:57, 1973); Kharash (J. Amer. Chem. Soc. 73:3240, 1951); Weinreb (Tet. Lett. 4171, 1977); Girard (J. Org. Chem. 48:3220, 1983); Lau (J. Org. Chem. 51:3038, 1986); Brederick et al. (Chem. Ber. p. 88, 1953); Friedman et al. (J. Org. Chem. 30:854, 1965); Dimroth et al. (Ber. 56:2602, 1956); Dimroth et al. (Ann. 634:102, 1961); Schulze et al. (Helv. Chimica Acta 74:1059, 1991); Mohammad Aslam et al. (J. Org. Chem. 56:5955–5958, 1991); Aliev et al. (Sulfur Lett. 12:123–132, 1991); Rutsch et al (Org. Coat. 8:175–195, 1986); Huang et al. (Tetrahedron Letts. 35:7204, 1994) and U.S. Pat. No. 4,321,118.

In another aspect, the invention encompasses compounds with selective COX-2 inhibitory activity of the general structure V:

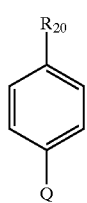
(V)

or a pharmaceutically acceptable salt thereof, wherein $R_{20}$ represents a $NHS(O)_2CH_3$, $S(O)_2CH_3$, $S(O)_2NH_2$, $S(O)(NH)NH_2$, or $S(O)_2NHC(O)(CH_2)_{1-3}CH_3$ group and Q represents one of the groups of the formulae Q(i) to Q(v) below:

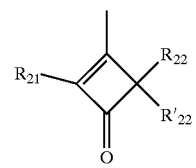
Q(i)

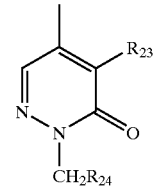
Q(ii)

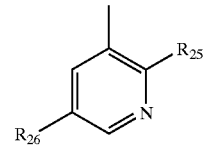
Q(iii)

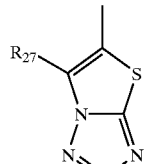
Q(iv)

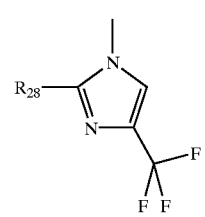
Q(v)

wherein $R_{21}$ represents a $C_{1-6}$-alkyl or $C_{3-7}$-Cycloalkyl group or an unsubstituted or mono-, di- or tri-substituted phenyl or naphthyl group wherein each potential substituent of the phenyl or naphthyl group is selected from the group consisting of halogen atom, $C_{1-6}$-alkyl, $C_{1-6}$-alkoxy, cyano and trifluoromethyl group, each of $R_{22}$ and $R'_{22}$ independently represents a hydrogen atom or $C_{1-6}$-alkyl group;

$R_{23}$ represents a hydrogen atom, trifluoromethyl, $C_{1-6}$-alkyl, hydroxy, or $C_{1-6}$-branched or unbranched alkoxy group;

$R_{24}$ represents a $C_{1-6}$-alkyl or $C_{3-7}$-cycloalkyl group or an unsubstituted or mono-, di- or tri-substituted phenyl group, each potential substituent of the phenyl group being selected from the group consisting of halogen atom, $C_{1-6}$-alkyl, $C_{1-6}$-alkoxy, cyano and trifluoromethyl groups;

$R_{25}$ represents a $C_{1-6}$-alkyl, $C_{3-7}$-cycloalkyl group or an unsubstituted, mono-, di- or tri-substituted aryl or heteroaryl group, wherein each potential substituent of the aryl or heteroaryl group is selected from the group consisting of halogen atom, $C_{1-6}$-alkyl, $C_{1-6}$-alkoxy, cyano and trifluoromethyl groups;

$R_{26}$ represents a hydrogen or halogen atom or a $C_{1-6}$-alkyl or $C_{1-6}$-alkoxy group;

$R_{27}$ represents a $C_{1-6}$-alkyl, $C_{3-7}$-cycloalkyl or an unsubstituted, mono-, di- or tri-substituted phenyl group, where each potential substituent for the phenyl group is selected from the group consisting of halogen atom, $C_{1-6}$-alkyl, $C_{1-6}$-alkoxy, cyano and trifluoromethyl groups; and $R_{28}$ represents an unsubstituted, mono-, di-, or tri-substituted heteroaryl group.

The following are independent preferences:

Preferred groups that $R_{20}$ may represent are $S(O)_2CH_3$ or $S(O)_2NH_2$.

Preferred groups that $R_{21}$ represents are phenyl, optionally substituted with 1–2 substituents chosen independently from the group consisting of halogen atom, methyl, ethyl, methoxy, ethoxy, and trifluoromethyl groups. More preferred is where $R_{21}$ represents a phenyl group, optionally substituted with 1–2 halogen atoms. Most preferable is where $R_{21}$ represents a phenyl group, optionally substituted with 1–2 fluorine atoms. Preferred alkyl groups that $R_{22}$ and $R'_{22}$ represent independently are methyl and ethyl groups. In a preferred embodiment, $R_{21}$ represents a phenyl group and each of $R_{22}$ and $R'_{22}$ is a methyl group.

Preferred alkyl groups that $R_{23}$ represents are methyl and ethyl. Preferred alkoxy groups that $R_{23}$ represents are methoxy, ethoxy, n-propoxy, and 2-propoxy. Preferred phenyl groups that $R_{24}$ represents are unsubstituted, mono-, di- or tri-substituted phenyl, wherein each potential substituent is selected from the group consisting of halogen atom, $C_{1-6}$-alkyl, $C_{1-6}$-alkoxy, cyano and trifluoromethyl. More preferred is where $R_{24}$ represents unsubstituted, mono- or di-substituted phenyl, wherein the potential substituents are halogen atoms. In a preferred aspect, $R_{23}$ represents 2-propoxy and $R_{24}$ represents phenyl.

A preferred group that $R_{25}$ represents is heteroaryl, optionally substituted with one or two substituents selected from the group consisting of halogen atoms, $C_{1-4}$-alkyl and $C_{1-4}$-alkoxy groups. More preferred is where the heteroaryl group that $R_{25}$ represents is pyridinyl, optionally substituted with a $C_{1-4}$-alkyl group. Most preferred is when $R_{25}$ represents a 2-methyl-5-pyridinyl group.

The preferred group that $R_{26}$ represents is halogen. More preferred is where $R_{26}$ is chlorine.

The preferred group that $R_{27}$ represents is phenyl, optionally substituted with 1–3 substituents each selected from the group consisting of halogen atom, $C_{1-6}$-alkyl and $C_{1-6}$-alkoxy groups. More preferred is where $R_{27}$ represents an unsubstituted phenyl group.

Preferred heteroaryl groups that $R_{28}$ represents are 3-pyridyl and 4-thiazolyl, optionally substituted with $C_{1-4}$-alkyl group. More preferred is where $R_{28}$ is selected from the group consisting of 3-(2-methylpyridinyl) and 4-(2-methylthiazolyl).

Preferred compounds of formula V include 3-(4-methylsulfonylphenyl)-2-(2-methyl-5-pyridyl)-5-chloro-pyridine, 1-(4-methylsulfonylphenyl)-2-(3-pyridyl)-4-trifluoromethyl-imidazole, 1-(4-sulfamoylphenyl)-2-(2-methyl-3-pyridyl)-4-trifluoromethyl-imidazole, and 1-(4-sulfamoylphenyl)-2-(2-methyl-4-thiazolyl)-4-trifluoromethyl-imidazole.

Syntheses of these compounds are described in WO 97/36863, WO 99/10331, Friessen et al. (Bioorgan. and Medic. Chem. Letts. 8:2777–2782, 1998), U.S. Pat. No. 5,552,422 and Khanna et al (J. Med. Chem. 43:3168–3185, 2000).

In another aspect the invention encompasses compounds of general formula VI

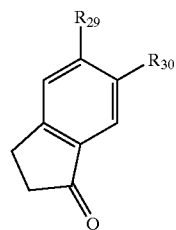

(VI)

or a pharmaceutically acceptable salt thereof, wherein $R_{29}$ represents a $NHS(O)_2CH_3$, $S(O)_2CH_3$, $S(O)_2NH_2$, $S(O)(NH)NH_2$, or $S(O)_2NHC(O)(CH_2)_{1-3}CH_3$ group, and $R_{30}$ represents a $C_{1-6}$-alkyl or $C_{3-7}$-cycloalkyl group or an unsubstituted or mono-, di- or tri-substituted phenyl or phenylthio group wherein each potential substituent for the phenyl or phenylthio group is selected from the group consisting of halogen atom, $C_{1-6}$-alkyl, $C_{1-6}$-alkoxy, cyano and trifluoromethyl groups.

The following are independent preferences:

The preferred groups that $R_{29}$ represents are $NHS(O)_2CH_3$, $S(O)_2CH_3$ or $S(O)_2NH_2$ groups. The preferred groups that $R_{30}$ represents are mono-, di- or tri-substituted phenyl or phenylthio group, wherein each substituent is selected from the group consisting of halogen atom, $C_{1-6}$-alkoxy and $C_{1-6}$-alkyl groups. More preferred is where $R_{30}$ represents a phenylthio group, wherein the phenyl moiety is optionally substituted with 1–3 halogen atoms. Also preferred is where $R_{30}$ represents a difluorophenylthio group. In a most preferred embodiment, $R_{29}$ represents $NHS(O)_2CH_3$ and $R_{30}$ represents 2,4-difluorophenylthio to yield the compound

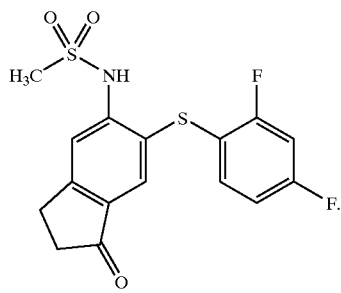

Syntheses of compounds of formula VI are described in international publication WO 94/13635. Additional relevant chemistry is described in U.S. Pat. No. 4,375,479.

The following definitions are adopted. Some definitions apply to all formulas presented herein, others apply to only some formulas presented herein, as will be apparent to a person of ordinary skill in the art.

As used herein, the term "alkyl", either alone or within other terms such as "haloalkyl" or "alkylsulfonyl" embraces linear or branched radicals having one to about twenty carbon atoms or, preferably, one to about twelve carbon atoms. Preferred alkyl radicals are "lower alkyl" radicals generally having one to about six carbon atoms, except as otherwise specified herein. Examples of such radicals include methyl, ethyl, n-propyl, isopropyl, n-butyl, isobutyl, sec-butyl, tert-butyl, pentyl, iso-amyl, hexyl and the like. The term "alkenyl" embraces linear or branched radicals having at least one carbon-carbon double bond of two to about twenty carbon atoms or, preferably, two to about twelve carbon atoms. Preferred alkyl radicals are "lower alkenyl" radicals, generally having two to about six carbon atoms, except as otherwise specified herein. Examples of such radicals include ethenyl, n-propenyl, butenyl, and the like. The term "halo" means halogens such as fluorine, chlorine, bromine or iodine atoms. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. Preferred haloalkyl radicals are "lower haloalkyl" radicals generally having 1–6 carbon atoms, except as otherwise specified herein. Examples of haloalkyl radicals include fluoromethyl, difluoromethyl, trifluoromethyl, chloromethyl, dichloromethyl, trichloromethyl, trichloroethyl, pentafluoroethyl, heptafluoropropyl, difluorochloromethyl, dichlorofluoromethyl, difluoroethyl, difluoropropyl, dichloroethyl and dichloropropyl. The term "hydroxyalkyl" embraces linear or branched alkyl radicals having one to about ten carbon atoms any one of which may be substituted with one or more hydroxyl radicals. Preferred hydroxyalkyl radicals are "lower hydroxyalkyl" radicals generally having one to six carbon atoms, except as otherwise specified herein, and one or more hydroxyl radicals. Examples of such radicals include hydroxymethyl, hydroxyethyl, hydroxypropyl, hydroxybutyl and hydroxyhexyl. The term "alkoxy" embraces linear or branched oxy-containing radicals having alkyl portions of one to about ten carbon atoms, such as methoxy radical. Preferred alkoxy radicals are "lower alkoxy" radicals generally having one to six carbon atoms, except as otherwise specified herein. Examples of such radicals include methoxy, ethoxy, propoxy, butoxy and tert-butoxy. The "alkoxy" radicals may be further substituted with one or more halo atoms, such as fluoro, chloro or bromo, to provide "haloalkoxy" radicals. Examples of such radicals include fluoromethoxy, chloromethoxy, trifluoromethoxy, trifluoroethoxy, fluoroethoxy and fluoropropoxy. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. The term "heterocyclic" embraces saturated, partially saturated and unsaturated heteroatom-containing ring-shaped radicals, where the heteroatoms may be selected from nitrogen, sulfur and oxygen. Examples of saturated heterocyclic radicals include saturated 3 to 6-membered heteromonocyclic groups containing 1 to 4 nitrogen atoms (e.g., pyrrolidinyl, imidazolidinyl, piperidino, piperazinyl, etc.); saturated 3 to 6-membered heteromonocyclic groups containing 1 to 2 oxygen atoms and 1 to 3 nitrogen atoms (e.g., morpholinyl, etc.); saturated 3 to 6-membered heteromonocyclic groups containing 1 to 2 sulfur atoms and 1 to 3 nitrogen atoms (e.g., thiazolidinyl, etc.). Examples of partially saturated heterocyclic radicals include dihydrothiophene, dihydropyran, dihydrofuran and dihydrothiazole. The term "heteroaryl" embraces unsaturated heterocyclic radicals. Examples of unsaturated heterocyclic radicals, also termed "heteroaryl" radicals include unsaturated 5 to 6 membered heteromonocyclic groups containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo [1,5-b] pyridazinyl, etc.), etc.; unsaturated 3 to 6-membered heteromonocyclic groups containing an oxygen atom, for example, pyranyl, 2-furyl, 3-furyl, etc.; unsaturated 5 to 6-membered heteromonocyclic groups containing a sulfur atom, for example, 2-thienyl, 3-thienyl, etc.; unsaturated 5- to 6-membered heteromonocyclic groups containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclic groups containing 1 to 2 oxygen atoms and 1 to 3 nitrogen atoms (e.g., benzoxazolyl, benzoxadiazolyl, etc.); unsaturated 5 to 6-membered heteromonocyclic groups containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclic groups containing 1 to 2 sulfur atoms and 1 to 3 nitrogen atoms (e.g., benzothiazolyl, benzothiadiazolyl, etc.) and the like. The term also embraces radicals where heterocyclic radicals are fused with aryl radicals. Examples of such fused bicyclic radicals include benzofuran, benzothiophene, and the like. Preferred heterocyclic radicals include five to ten membered fused or unfused radicals. More preferred examples of heteroaryl radicals include benzofuryl, 2,3-dihydrobenzofuryl, benzothienyl, indolyl, dihydroindolyl, chromanyl, benzopyran, thiochromanyl, benzothiopyran, benzodioxolyl, benzodioxanyl, pyridyl, thienyl, thiazolyl, oxazolyl, furyl, and pyrazinyl. The terms "N-alkylamino" and "N,N-dialkylamino", whether alone or linked to other terms such as "alkylaminocarbonyl" or "alklyaminosulfonyl" denote amino groups which have been substituted with one alkyl radical and with two alkyl radicals, respectively. More preferred alkylamino radicals are "lower alkylamino" radicals having one or two lower alkyl radicals, attached to a nitrogen atom. Suitable "alkylamino" may be mono or dialkylamino such as N-methylamino, N-ethylamino, N,N-dimethylamino, N,N-diethylamino or the like. The term "sulfonyl", whether used alone or linked to other terms such as alkylsulfonyl, denotes the radical —SO$_2$—. "Alkylsulfonyl" embraces alkyl radicals attached to a sulfonyl radical, where alkyl is defined as above. More preferred alkylsulfonyl radicals are "lower alkylsulfonyl" radicals having lower alkyl radicals attached to a sulfonyl radical. Examples of such lower alkylsulfonyl radicals include methylsulfonyl, ethylsulfonyl and propylsulfonyl. The terms "sulfamyl" and "aminosulfonyl", whether alone or used with terms such as "N-alkylaminosulfonyl", "N-arylaminosulfonyl" and "N,N-dialkylaminosulfonyl", denotes a sulfonyl radical substituted with an amine radical, forming a sulfonamide (—SO$_2$NH$_2$). The terms "N-alkylaminosulfonyl" and "N,N-dialkylaminosulfonyl" denote sulfamyl radicals substituted, respectively, with one alkyl radical, or two alkyl radicals attached to the nitrogen atom. More preferred alkylaminosulfonyl radicals are "lower alkylaminosulfonyl" radicals having lower alkyl radicals attached to the nitrogen atom. Examples of such lower alkylaminosulfonyl radicals include N-methylaminosulfonyl, N-ethylaminosulfonyl and N-methyl-N-ethylaminosulfonyl. The term "carbonyl", whether used alone or with other terms, denotes —(C=O)—. The term "aminocarbonyl" when used by itself or with other terms such as "N-alkylaminocarbonyl" or "N,N-dialkylaminocarbonyl" denotes an amide group of the formula —C(=O)NH$_2$. The terms "N-alkylaminocarbonyl" and "N,N-dialkylaminocarbonyl" denote aminocarbonyl radicals which have been substituted on the nitrogen atom with one alkyl radical and with two alkyl radicals, respectively. More preferred are "lower alkylaminocarbonyl" having lower alkyl radicals as described above attached to an aminocarbonyl radical. The term "N-cycloalkylaminocarbonyl" denotes aminocarbonyl radicals which have been substituted on the nitrogen atom with at least one cycloalkyl radical. More preferred are "lower cycloalkylaminocarbonyl" having lower cycloalkyl radicals of three to seven carbon atoms, attached to an aminocarbonyl radical. The term "aralkyl" embraces aryl-substituted alkyl radicals. Preferable aralkyl radicals are "lower aralkyl" radicals having aryl radicals attached to a lower alkyl radical. Examples of such radicals include benzyl, diphenylmethyl, triphenylmethyl, phenylethyl and diphenylethyl. The terms benzyl and phenylmethyl are interchangeable. The term "cycloalkyl" embraces radicals having three to ten carbon atoms. More preferred cycloalkyl radicals are "lower cycloalkyl" radicals having three to seven carbon atoms. Examples include radicals such as cyclopropyl, cyclobutyl, cyclopentyl, cyclohexyl and cycloheptyl. The term "cycloalkenyl" embraces unsaturated cyclic radicals having three to ten carbon atoms, such as cyclobutenyl, cyclopentenyl, cyclohexenyl and cycloheptenyl. The term "alkylthio" embraces radicals containing a linear or branched alkyl radical, of one to ten carbon atoms, attached to a divalent sulfur atom. An example of "alkylthio" is methylthio, (CH$_3$—S—). The term "arylthio" embraces aryl radicals of six to ten carbon atoms, attached to a divalent sulfur atom. An example of "arylthio" is phenylthio. The term "haloaralkyl" embraces aryl radicals as defined above attached to haloalkyl radicals. The term "aminocarbonylhaloalkyl" embraces aminocarbonyl radicals as defined above substituted on a haloalkyl radical. The term "cycloalkylalkyl" embraces cycloalkyl radicals having three to ten carbon atoms attached to an alkyl radical, as defined above. More preferred cycloalkylalkyl radicals are "lower cycloalkylalkyl" radicals having cycloalkyl radicals attached to lower alkyl radicals as defined above. Examples include radicals such as cyclopropylmethyl, cyclobutylmethyl, and cyclohexylethyl.

In another aspect, the invention provides methods for treating neuromuscular dysfunction of the lower urinary tract in mammals that involve administering to affected mammals effective amounts of a compound that:
(a) significantly inhibits a COX-2 isozyme; and
(b) exhibits a potency for the COX-2 isozyme that is at least 10-fold greater, and preferably at least 100-fold greater, than the inhibitory potency said compound exhibits for the COX-1 isozyme.

Systems for ascertaining whether these criteria are met are described below.

Preferably, compounds to be used in practicing the present invention should inhibit COX-2 isozyme with an IC$_{50}$ of from about 0.1 to about 100 nM in the models given in Examples 1 and 2.

Administration of the selective COX-2 inhibitors, their stereoisomers, pharmaceutically acceptable salts, hydrates or solvates may be achieved by any effective route, including oral, enteral, intravenous, intramuscular, subcutaneous, transmucosal, and by inhalation routes. Preferable means of administration are via an oral or transdermal route.

Also provided are pharmaceutical formulations comprising the compounds described above in conjunction with pharmaceutically acceptable carriers and/or excipients.

In yet another aspect, the invention provides a method for identifying a compound useful for treating neuromuscular dysfunction of the lower urinary tract. The method is carried out using the steps of:
(a) individually measuring the inhibitory effects of test compounds on COX-2 and COX-1 isozymes; and
(b) identifying those test compounds that
(1) inhibit the COX-2 isozyme with an IC$_{50}$ at or below concentrations of $10^{-7}$ M and
(2) inhibit the COX-1 isozyme with an IC$_{50}$ that is at least about 10-fold higher than the IC$_{50}$ the compound exhibits for the COX-2 isozyme.

Preferably, the activity of compounds identified in step (b) above is confirmed by evaluating the inhibition of volume-induced rhythmic bladder voiding contractions in anaesthetized rats (see Example 3).

DETAILED DESCRIPTION OF THE INVENTION

All U.S. patents, patent applications and other publications and cited herein are hereby incorporated by reference in their entirety. In the case of inconsistencies in definitions, the present description will control.

It is further understood that all compounds described, listed and represented herein are meant to include all hydrates, solvates, polymorphs and pharmaceutically acceptable salts thereof.

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

The invention provides methods and compositions for treatment of neuromuscular dysfunction of the lower urinary tract, particularly those involving micturition (urination) disorder, such as dysuria, incontinence, and enuresis. The methods involve administering to affected individuals selective COX-2 inhibitors for a sufficient time and in an amount effective for lessening or ameliorating at least one symptom of the micturition disorder. Such symptoms include but are not limited to filling symptoms, urgency, incontinence and nocturia, as well as voiding problems such as weak stream, hesitance, intermittency, incomplete bladder emptying and abdominal straining.

As used herein, a "mammal in need" of treatment of neuromuscular dysfunction of the lower urinary tract is a mammal exhibiting one or more symptoms of a micturition disorder, such as those listed above.

The term "treatment" is defined as the prevention, lessening, or amelioration of at least one of the foregoing symptoms of neuromuscular dysfunction of the lower urinary tract.

The term "exposing lower urinary tract tissue" is defined as causing said tissue to come in contact with a selective COX-2 inhibitor of the invention. The term encompasses, without limitation, direct application of a selective COX-2 inhibitor to lower urinary tract tissue. The term also encompasses, again without limitation, dissolving a selective COX-2 inhibitor in a solution that is in contact with lower urinary tract tissue. Also encompassed without limitation is the instance where a selective COX-2 compound or composition thereof is administered to a mammal and the selective COX-2 inhibitor is subsequently transported through the body, e.g., through normal circulation, to lower urinary tract tissue, thereby contacting the tissue.

Efficacy of treatment may be determined by any method known in the art. Such methods include but are not limited determining voiding volumes, frequency of urination, and frequency and strength of bladder contractions in individuals with neuromuscular dysfunction of the lower urinary tract; or and interviewing such individuals to determine if they have experienced the amelioration of any such symptom. Other measures of efficacy include a measurable reduction, most preferably a clinically relevant reduction, of urine leakage related to feelings of urgency, urine leakage related to physical activity, coughing or sneezing, leakage of small amounts of urine (drops), difficulty in bladder emptying, general leakage not related to urgency or activity, nighttime urination, bedwetting, a feeling of incomplete bladder emptying, etc.

The use of patient-questionnaires and scales to measure symptom severity is widely accepted, complementing objective clinical measures and having the advantage of being inexpensive and potentially self-administered. Female and male lower urinary tract questionnaires have been developed which provide a method of measuring symptom severity and life quality in a reproducible and valid fashion as well as allowing an in-depth assessment of specific lower urinary tract symptoms. Sum of scores collected for the questions included in the questionnaires are highly correlated with subjects' ratings of the magnitude of their urinary problems, and are very sensitive to changes induced by treatment (Barry et al., J. Urol., 148:1549–1557, 1992; Jackson et al., Brit. J. Urol., 77:805–812, 1996).

Selective COX-2 inhibitors suitable for use in practicing the present invention include without limitation those compounds having one or more of the following properties:

(1) Significant COX-2 inhibitory activity: Useful compounds preferably exhibit inhibitory potency ($IC_{50}$) between 100 and 0.1 nM. Without limiting the present disclosure, as described in more detail below, potency may be measured by determining the $IC_{50}$ of compounds in vivo or in vitro, including cell extracts or fractions of extracts. Iihibitory potency may also be determined using, as non-limiting examples, native or recombinant COX-2 enzymes, enzymes that are expressed constitutively or that have been induced, and enzymes that have expressed in native or non-native species and/or cell types.

(2) Selectivity: Preferred compounds exhibit at least about 10-fold greater potency in inhibiting the COX-2 isozyme compared to the COX-1 isozyme. More preferred are compounds that exhibit about 100-fold greater potency in inhibiting the COX-2 isozyme compared to the COX-1 isozyme.

Accordingly, compounds belonging to this general class are suitable candidates for testing according to the methods taught below.

Compounds that selectively inhibit COX-2 isozyme are therefore candidates for screening to identify compounds useful in treating neuromuscular dysfunction of the lower urinary tract and are exemplified without limitation by:

Compound A:

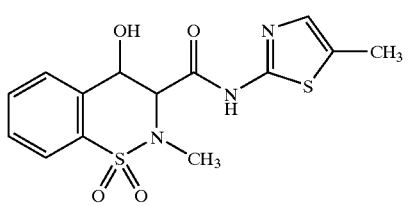

(A)

Compound B:

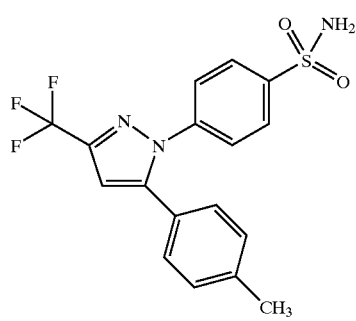

(B)

Compound C:

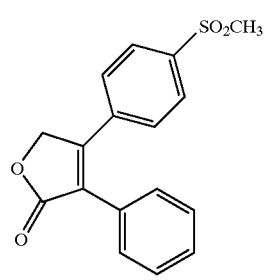

(C)

Compound D:

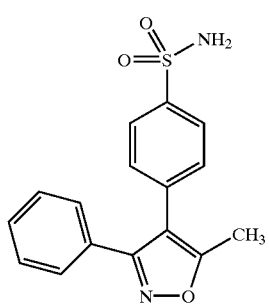

(D)

Compound E:

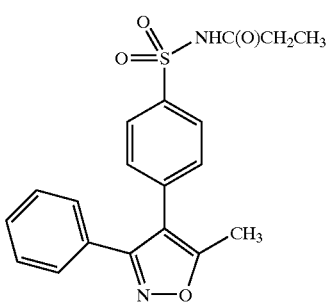

(E)

These compounds can be synthesized as described in:
U.S. Pat. No. 4,233,299 for A and related compounds;
International publication WO 95/15316 for B and related compounds;
U.S Pat. No. 5,474,995 for C and related compounds;
U.S. Pat. No. 5,633,272 for D and related compounds; and
International publication WO 97/38986 for E and related compounds.

Screening candidate compounds to identify those compounds that are useful in practicing the present invention involves:
1) evaluating their potency and selectivity in inhibiting the COX-2 and COX-1 isozymes; and
2) confirming their pharmacological activity using one or more animal model systems for neuromuscular dysfunction of the lower urinary tract.

To compare the inhibition of COX-1 and COX-2 by various compounds, numerous assays have been developed. The results from these assays are used to calculate a measure of COX-2 selectivity, and compounds are then compared to each other by ranking their COX-2 selectivity.

The commonly used in vitro assays for assessing inhibition of COX-1 and COX-2 can be divided into two groups. The first consists of measuring the effect of inhibitors in assays of non-recombinant enzymes purified or partially purified from animal cells, or non-recombinant enzymes that are present in extracts or extract-fractions from animal cells or cell lines. These were the first tests to be developed and are historical in nature. The second type of assay uses human recombinant enzymes that have been expressed in human cell lines or human blood cells, typically platelets and monocytes. These are the current standard tests (Pairet et al., in *Clinical Significance and Potential of Selective COX-2 Inhibitors*, Vane, J. R. and Butting, R. M. (eds.), W. Harvey Press, pp. 19–30, 1998).

The COX enzymes used in these assays can be of animal or human origin, they can be native or recombinant, and they can be used either as purified enzymes, microsomal preparations or whole cell assays. In addition, prostaglandin synthesis can be measured either from endogenously released arachidonic acid or from exogenously added arachidonic acid. In assays using recombinant COX-1 and COX-2 enzymes, the expression system used for gene replication and expression also varies. Not all assay systems require a COX-2 inducing agent. For instance, cells may be transfected with recombinant enzymes that are expressed constitutively. In other cell types, however, steps may be required to induce COX-2. In such cases, COX-2 is usually induced with either lipopolysaccharide (LPS) or cytokines, such as interleukin-1 (IL-1) or tumor necrosis factor (Pairet et al., in *Clinical Significance and Potential of Selective COX-2 Inhibitors*, Vane, J. R. and Butting, R. M. (eds.), W. Harvey Press, pp. 19–30, 1998).

In a preferred embodiment, measurement of inhibition of COX isozymes is performed in stably transfected Chinese hamster ovarian (CHO) cells expressing either human COX-1 or COX-2, as previously described (Riendeau et al., Br. J. Pharmacol. 121:105, 1997; Elrich et al., Clin. Pharm. Ther. 65: 336, 1999). Also preferred is where inhibition of COX isozymes is measured on constitutive and inducible forms of human cyclooxygenase (hCOX) cloned and expressed in insect cells (*Spodoptera frugiperda*), utilizing a baculovirus expression system. Expression of COX protein is determined by assessing PG-synthetic capability in homogenates from insect cells (Sf9 cells) incubated for 3 days with COX-1 or COX-2 recombinant baculovirus as previously described (Gierse et al., Biochem. J. 305: 479, 1995).

The inhibitory activity of a test compound can be measured for different isozymes, and the concentration inhibiting the enzyme activity by 50% ($IC_{50}$) can be calculated using regression analysis, or equivalent computational methods that are well-known in the art (Tallarida et al., Manual of Pharmacologic Calculations. Springer-Verlag, pp. 10–12, 1981.)

As discussed above, compounds useful in practicing the present invention inhibit the COX-2 isozyme with an $IC_{50}$ of below 100 nM with at least about 10-fold, and preferably about 100-fold, higher potency for the COX-2 isozyme versus the COX-1 isozyme. It will be understood that measurements of inhibitory potency of a particular compound may vary depending upon the source of isozymes, as well as specific assay conditions.

To control for this type of variability, Compound A can be included in all assays as a standardization control. That is, the values of $IC_{50}$ obtained for compound A are compared to the values obtained with tested compounds for each assay. This allows a direct comparison of neurons absolute potency in inhibiting COX isozymes and ratios of inhibitory activities between different assays for the purpose of assessing whether the compound is within the scope of the invention.

A compound is considered to be a "selective" COX-2 inhibitor if it exhibits a selectivity ratio of at least 10-fold, i.e., the $IC_{50}$ for COX-2 is at least 10-fold below the $IC_{50}$ for COX-1.

Once a compound is identified as possessing selectivity for the COX-2 isozyme, its pharmacological activity can be confirmed using one or more animal model systems for neuromuscular dysfunction of the lower urinary tract.

A useful animal model system for measuring such pharmacological activity is, without limitation, volume-induced rhythmic bladder voiding contractions in anesthetized rats. In this method, the urinary bladder is catheterized through the external urethra with a polyethylene tubing filled with physiological saline. The external urethra is then ligated and connected to a pressure recording device. The bladder is then filled with saline until reflex voiding contractions occur, after which the frequency of the voiding contractions is measured for 15 min. Test compounds are then administered intravenously and their effect evaluated for the following 60 min. This method is described in more detail in Example 3 below, and was originally used to validate the predictive qualities of the selective COX-2 inhibitors for the foregoing urinary tract disorders. This model has been validated by the use of different reference standards (Guarneri et al., Pharmacol. Res. 27:173–187, 1993).

Therapeutic Applications

The invention encompasses pharmaceutical formulations comprising those listed above, as well as methods employing these formulations for treating neuromuscular dysfunction of the lower urinary tract such as dysuria, incontinence, and enuresis. Dysuria includes urinary frequency, nocturia, urgency, and difficulty in emptying the bladder, i.e., a suboptimal volume of urine is expelled during micturition. Incontinence syndromes include stress incontinence, urgency incontinence, and overflow incontinence. Enuresis refers to the involuntary passage of urine at night or during sleep. Without wishing to be bound by theory, it is believed that administration of selective COX-2 inhibitors prevents unwanted activity of the bladder afferent neurons and/or inhibits the pontine micturition center controlling micturition. Thus it is contemplated that a wide range of neuromuscular dysfunction of the lower urinary tract can be treated using the compounds of the present invention.

An "effective amount" of the compound for treating a urinary disorder is an amount that results in measurable amelioration of at least one symptom or parameter of the disorders described above.

An effective amount for treating the disorder can easily be determined by empirical methods known to those of ordinary skill in the art, such as by establishing a matrix of dosages and frequencies of administration and comparing a group of experimental units or subjects to each point in the matrix. The exact amount to be administered to a patient will vary depending on the state and severity of the disorder and the physical condition of the patient. A measurable amelioration of any symptom or parameter can be determined by a physician skilled in the art or reported by the patient to the physician. It will be understood that any clinically or statistically significant attenuation or amelioration of any symptom or parameter of urinary tract disorders is within the scope of the invention. Clinically significant attenuation or amelioration means perceptible to the patient and/or to the physician or other practitioner.

For example, a single patient may suffer from several symptoms of dysuria simultaneously, such as, for example, urgency and frequency, either or both of which may be reduced using the methods of the present invention. In the case of incontinence, any reduction in the frequency or volume of unwanted passage of urine is considered a beneficial effect of the present methods of treatment, and thus, an amelioration of a symptom.

The pharmaceutical compositions of the present invention comprise a compound of the invention as an active ingredient or a pharmaceutically acceptable salt, thereof, and may also contain a pharmaceutically acceptable carrier and optionally other therapeutic ingredients.

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing a compound of the invention are employed. (For purposes of this application, topical application shall include mouth washes and gargles.)

Dosage levels of the order of from about 0.01 mg to about 140 mg/kg of body weight per day are useful in the treatment of the above-indicated conditions, or alternatively about 0.5 mg to about 7 g per patient per day. For example, the above-indicated conditions may be effectively treated by the administration of from about 0.01 to about 50 mg of the compound per kilogram of body weight per day, or alternatively about 0.5 mg to about 3.5 g per patient per day. Preferably the agent is administered in a dosage from about 0.1 to about 15 mg of the compound per kilogram of body weight per day and most preferably from about 0.2 to 6 mg of the compound per kilogram of body weight per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, for example 5 mg, 12.5 mg, 25 mg, 50 mg, 100 mg, 200 mg, 300 mg, 400 mg or 500 mg.

It will be understood that the pharmaceutical formulations of the invention need not in themselves contain the entire amount of the agent that is effective in treating the disorder, as such effective amounts can be reached by administration of a plurality of doses of such pharmaceutical formulations.

It will be understood that the specific dose level for any particular patient will depend upon a variety of factors including the age, body weight, general health, sex, diet, time of administration, route of administration, rate of excretion, drug combination, the severity of the particular disease undergoing therapy and the activity of the administered compound.

The methods, tables and examples provided below are intended to more fully describe preferred embodiments of the invention and to demonstrate its advantages and applicability without limiting its scope.

EXAMPLE 1

Measurement of Inhibition of COX-2 and COX-1 Isozymes in CHO Cells

Measurement of inhibition of COX isozymes can be performed in stably transfected Chinese hamster ovarian (CHO) cells expressing either human COX-1 or COX-2, as previously described (Riendeau et al., Br. J. Pharmacol. 121:105, 1997; Elrich et al., Clin. Pharm. Ther. 65: 336, 1999).

Cells ($0.3 \times 10^6$ cells in 200 $\mu$l) are preincubated in Hank's Balanced Salts Solution (HBSS) containing 15 mM HEPES, pH 7.4, with 3 $\mu$l of the test drug or DMSO vehicle for 15 min at 37° C. before challenge with arachidonic acid. Cells are challenged for 15 min with an arachidonic acid solution (Stock solution is 100 $\mu$M (for COX-2) or 5 $\mu$M (for COX-1) arachidonic acid, 10% ethanol in HBSS) to yield final concentrations of 10 $\mu$M arachidonic acid in the CHO[COX-2] assay and of 0.5 $\mu$M arachidonic acid in the CHO[COX-1] assay. In the absence of exogenous arachidonic acid, levels of $PGE_2$ in samples from CHO[COX-1] and CHO[COX-2] cells were <80 pg $PGE_2$ per $10^6$ cells. In the presence of 0.5 $\mu$M exogenous arachidonic acid, levels of $PGE_2$ in samples from CHO[COX-1] cells increased to 300–2300 pg $PGE_2$ per $10_6$ cells, whereas in the presence of 10 $\mu$M exogenous arachidonic acid, levels of $PGE_2$ in samples from CHO [COX-2] cells increased to 500–1400 pg $PGE_2$ per $10_6$ cells.

Cyclooxygenase activity in the absence of test compounds was determined as the difference in $PGE_2$ levels of cells challenged with arachidonic acid versus the $PGE_2$ levels in cells mock-challenged with buffer containing ethanol. Each experiment included a set of 8 positive and negative control samples (±arachidonic acid challenge) for cells preincubated in the absence of inhibitor. Compounds were typically tested at 8 concentrations in duplicate with 3 fold serial dilutions in DMSO. Inhibition of $PGE_2$ synthesis by test compounds was calculated as a percentage of the activity in the presence of drug versus the activity in the positive control samples.

EXAMPLE 2

Measurement of Inhibition of COX-2 and COX-1 Isozvmes in Sf9 Cells

Constitutive and inducible forms of human cyclooxygenase (hCOX) were cloned and expressed in insect cells (*Spodoptera fiugiperda*), utilizing a baculovirus expression system (Gierse et al., Biochem. J. 305: 479, 1995). Expression of COX protein was determined by assessing PG-synthetic capability in homogenates from insect cells (Sf9 cells) incubated for 3 days with COX-1 or COX-2 recombinant baculovirus as previously described (Gierse et al., Biochem. J. 305: 479, 1995).

Cells expressing hCOX-1 or hCOX-2 were homogenized and incubated with arachidonic acid (10 $\mu$M). COX activity was determined by monitoring PG production. No COX activity was detected in mock-infected Sf9 cells. Test compounds (0.001–100 $\mu$M) were preincubated with crude 1% CHAPS homogenates (2–10 $\mu$g of protein) for 10 min before addition of arachidonic acid. $PGE_2$ formed was detected by ELISA, following 10 min incubation.

As shown in Table 1 below, compounds A to C were potent and selective inhibitors of the COX-2 isozyme, but showed undetectable or markedly reduced inhibitory activity of the COX-1 isozyme. Indomethacin was confirmed as a non selective COX inhibitor.

TABLE 1

Inhibition of COX-2 and COX-1 isozymes transfected in different cells by tested compounds
Data represents the $IC_{50}$ (concentration inhibiting enzymatic activity by 50%)
values ($\mu M$) taken from the cited literature.

| Tested Compound | COX-2 | COX-1 | COX-1/ COX-2 | Cell type | Reference |
|---|---|---|---|---|---|
| Compound A | 0.006 | 1.810 | 302 | CHO | A |
| Compound B | 0.040 | 15.000 | 375 | Sf9 | B |
| Compound C | 0.018 | >15.000 | >833 | CHO | C |
| Indomethacin | 0.026 | 0.018 | 0.7 | CHO | A |

A = Riendeau et al., Br. J. Pharmacol. 121:105, 1997
B = Penning et al., J. Med. Chem. 40:1347, 1997
C = Elrich et al., Clin. Pharm. Ther. 65:336, 1999.

EXAMPLE 3

Effects of Test Compounds on Volume-Induced Rhythmic Bladder Voiding Contractions in Anaesthetized Rats Female Sprague Dawley rats weighing 225–275 g (Crl: CD° BR, Charles River Italia) were used. The animals were housed with free access to food and water and maintained on a 12 h alternating light-dark cycle at 22–24° C. for at least one week, except during the experiment. The activity on the rhythmic bladder voiding contractions was evaluated according to the method of Dray (J. Pharmacol. Methods, 13:157, 1985), with some modifications as in Guarneri (Pharmacol. Res., 27: 173, 1993). Briefly, rats were anesthetized by subcutaneous injection of 1.25 g/kg (5 ml/kg) urethane, after which the urinary bladder was catheterized via the urethra using PE 50 polyethylene tubing filled with physiological saline. The catheter was then tied in place with a ligature around the external urethral orifice and connected to a conventional pressure transducer (Statham P23 ID/P23 XL). The intravesical pressure was displayed continuously on a chart recorder (Battaglia Rangoni KV 135 with DC1/TI amplifier). The bladder was then filled via the recording catheter with incremental volumes of warm (37° C.) saline until reflex bladder voiding contractions occurred (usually upon addition of 0.8–1.5 ml saline). After 15 min the test compounds were administered by intravenous (i.v.) route. For i.v. administration of bioactive compounds, a PE 50 polyethylene tubing filled with physiological saline was inserted into the jugular vein.

Bioactivity was assessed in individual animals (using 6–10 rats per dose) by measuring the duration of bladder quiescence (i.e., the duration of time during which no contractions occurred) over a 60 min period. To compare the potency of the tested compounds in inhibiting the bladder voiding contractions, effective doses that prevented bladder contraction for 10 minutes ($ED_{10min}$) were evaluated by linear regression analysis.

The distension of the urinary bladder in urethane-anaesthetized rats produced a series of rhythmic bladder voiding contractions whose characteristics have been described (Guarneri et al., Pharmacol. Res., 27:173, 1993). Compounds A-C inhibited the voiding contractions, inducing a dose-dependent block of the bladder contractions lasting, at the highest dose tested, up to 34 min. The potency of some selective COX-2 inhibitors in inhibiting bladder voiding contractions (expressed as the dose calculated to induce 10 min of bladder quiescence, i.e., $ED_{10min}$) was similar (e.g.,. Compound B) or slightly lower (e.g. Compound C) to that of morphine, a drug acting mainly at the level of the central nervous system.

Indomethacin proved less potent than the selective COX-2 inhibitors.

The results are shown in Table 2 below.

The results presented in Table 1 and Table 2 demonstrate that Compounds A to C were ineffective inhibitors if the COX-1 isozyme but were very potent inhibitors of both the COX-2 isozyme and bladder voiding contractions. Potency in inhibiting voiding contractions, therefore, was highly correlated with potency in inhibiting the COX-2 isozyme, but was not correlated with potency of COX-1 inhibition.

TABLE 2

Effects of COX inhibitors on rhythmic bladder voiding contractions after intravenous administration.
Data represent the mean values ± S.E. of the duration of bladder quiescence (absence of contracions in min.) The $ED_{10\ min}$ values represent the dose inducing a 10 min of absence of bladder contractions, evaluated by linear regression analysis.

| | Dose (mg/kg i.v.) | Bladder quiescence (min ± S.E.) |
|---|---|---|
| Compound A | 0.1 | 5.12 ± 1.59 |
| | 0.3 | 11.50 ± 3.99 |
| | 1.0 | 22.52 ± 5.55 |
| | 3.0 | 34.24 ± 13.03 |
| | $ED_{10\ min}$ = 0.208 mg/kg | |
| Compound B | 0.01 | 4.05 ± 0.68 |
| | 0.10 | 10.53 ± 2.04 |
| | 1.0 | 28.35 ± 5.19 |
| | $ED_{10\ min}$ = 0.044 mg/kg | |
| Compound C | 0.03 | 3.75 ± 0.96 |
| | 0.10 | 4.85 ± 1.80 |
| | 0.30 | 16.44 ± 6.13 |
| | $ED_{10\ min}$ = 0.135 mg/kg | |
| Indomethacin | 0.3 | 4.39 ± 1.08 |
| | 1.0 | 7.91 ± 1.79 |
| | 3.0 | 35.00 ± 5.78 |
| | $ED_{10\ min}$ = 0.652 mg/kg | |
| Morphine | 0.01 | 2.76 ± 0.93 |
| | 0.03 | 6.89 ± 2.11 |
| | 0.10 | 13.83 ± 2.40 |
| | 0.30 | 18.17 ± 3.60 |
| | $ED_{10\ min}$ = 0.050 mg/kg | |

Summarizing, compounds A to C were found to be selective inhibitors of COX-2 isozyme, exhibiting an inhibitory potency nearly equal to indomethacin (a non selective COX inhibitor) on this isoform of cyclooxygenase, and ineffective inhibitors of the COX-1 isozyme. Compounds A to C were further found to be more potent than indomethacin in inhibiting bladder voiding contraction in anaesthetized rats. The frequency of bladder voiding contractions in anaesthetized rats is related to the sensory afferent arm of reflex micturition and to the integrity of the micturition center (Maggi et al., Brain Res., 415: 1, 1987; Maggi et al, J. Urol., 136:696, 1986). Taking into account the lack of effects of these compounds on the COX-1 isozyme and the presence of constitutive expression of COX-2 in the central nervous system, it is possible that these compounds act at the level of the micturition center to prevent bladder contraction.

EXAMPLE 4

Effects of Test Compounds in Patients Suffering from Lower Urinary Tract Symptoms The efficacy of compounds A, B and C in treating lower urinary tract symptoms is tested in patients. Compounds A, B or C are administered orally 1–2 times per day in doses of 5, 12.5, 25 or 100 mg, for a period of 40 days. Daily dosages total 5, 10, 12.5, 25, 50, 100 or 200 mg.

The therapeutic effect of compounds A, B or C is measured by patient questionnaires, which are used to determine, e.g., urinary frequency, nocturia, urgency, difficulty with voiding, and pain or discomfort in lower abdominal or genital areas. Effectiveness of compounds A, B or C is measured in amelioration of any symptom associated with LUTS, as compared to a control patient group that is administered placebo, according to the same regimen.

EXAMPLE 5

Effects of Test Compounds in Patients Suffering from Lower Urinary Tract Symptoms The efficacy of compounds D and E in treating lower urinary tract symptoms is tested in patients using the protocol described in Example 4.

What is claimed is:

1. A method of treating neuromuscular dysfunction of the lower urinary tract in a mammal in need of such treatment comprising administering to said mammal a therapeutically effective amount of a COX-2 selective compound of the general formula I,

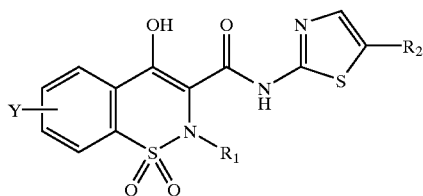

(I)

or a pharmaceutically acceptable salt thereof, wherein, $R_1$ represents a hydrogen atom or a methyl or ethyl group, $R_2$ represents a methyl, ethyl or n-propyl group, and Y represents a hydrogen, fluorine or chlorine atom or a methyl or methoxy group.

2. The method of claim 1 wherein said mammal is a human.

3. The method of claim 1 wherein the administered compound is 1, 1-dioxo-4-hydroxy-2-methyl-N-(5-methyl-2-thiazolyl)-2H-1,2-benzothiazine-3-carboxamide (Compound A).

4. A method of treating neuromuscular dysfunction of the lower urinary tract in a mammal in need of such treatment, comprising administering to said mammal a therapeutically effective amount of a COX-2 selective compound of the general formula II,

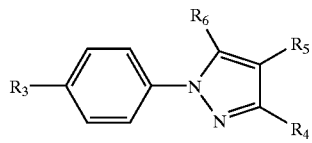

(II)

or pharmaceutically acceptable salt thereof, wherein, $R_3$ represents $NHS(O)_2CH_3$, $S(O)_2CH_3$, $S(O)_2NH_2$, $S(O)(NH)NH_2$, or $S(O)_2NHC(O)(CH_2)_{1-3}CH_3$;

$R_4$ represents a halogen atom or a haloalkyl, cyano, nitro, aminocarbonyl, N-alkylaminocarbonyl, N,N-dialkylaminocarbonyl, cycloalkylaaminocarbonyl, haloaralkyl, aminocarbonylhaloalkyl, alkylsulfonyl, or N-alkylaminosulfonyl group;

$R_5$ represents a hydrogen or halogen atom or an alkyl, thio, alkylthio, haloalkyl, cyano, hydroxyalkyl, alkylsulfonyl or cycloalkyl group; and $R_6$ represents an aryl, cycloalkyl, cycloalkenyl or heterocyclic group and is optionally substituted with one or more radicals selected from the group consisting of halogen atom, alkylthio, alkyl, alkenyl, alkylsulfonyl, cyano, aminocarbonyl, haloalkyl, hydroxyl, alkoxy, hydroxyalkyl, haloalkoxy, sulfamyl, amino, heterocyclic, cycloalkylalkyl and nitro group; or $R_5$ and $R_6$ together with the pyrazole ring atoms to which they are attached form a 6- or 7-membered ring in which the atom in the 6- or 7-membered ring that is next to the 4-position of the pyrazole ring is a sulfur atom, the 6- or 7-membered ring being optionally fused to a benzene ring which itself may be substituted with one or more substituents selected from the group consisting of halogen atom and $C_{1-4}$ alkyl group.

5. The method of claim 4 wherein said mammal is a human.

6. The method of claim 4 wherein the administered compound has a formula where $R_3$ represents $S(O)_2NH_2$.

7. The method of claim 4 wherein the administered compound has a formula where $R_4$ represents a fluorine atom or a trifluoromethyl group.

8. The method of claim 4 wherein the administered compound has a formula where $R_5$ represents a hydrogen or halogen atom.

9. The method of claim 4 wherein the administered compound has a formula where $R_6$ represents a phenyl group, optionally substituted with one or more substituent selected from the group consisting of halogen atoms, $C_{1-4}$-alkyl, $C_{2-4}$-alkenyl, aminocarbonyl, $C_{1-4}$ haloalkyl, hydroxyl, $C_{1-4}$alkoxy, hydroxyalkyl, haloalkoxy, and amino groups.

10. The method of claim 9 wherein the administered compound has a formula where $R_{6\ 1006}$ is a p-tolyl group.

11. The method of claim 4 wherein the administered compound has a formula where $R_4$ represents a trifluoromethyl group, $R_5$ represents a hydrogen atom, and $R_6$ represents a para-substituted phenyl group.

12. The method of claim 4 wherein the administered compound is 1-(4-sulphamoylphenyl)-3-trifluoromethyl-5-(p-tolyl)-pyrazole (Compound B).

13. The method of claim 4 wherein $R_5$ and $R_6$ together with the carbon atoms of the pyrazole ring to which they are attached form a six membered sulfur-containing heterocyclic ring which is further fused to a substituted benzene ring as represented by the structure

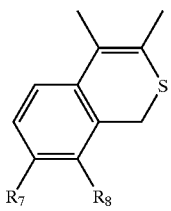

wherein $R_7$ represents a $C_{1-4}$ lower alkoxy group and $R_8$ represents a halogen atom.

14. The method of claim 13 wherein the administered compound has the structure represented by the formula

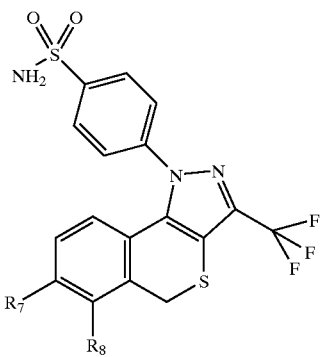

wherein $R_7$ represents a $C_{1-4}$ lower alkoxy group and $R_8$ represents a halogen atom.

15. The method of claim 14 wherein the administered compound has a formula where $R_7$ is methoxy.

16. The method of claim 14 wherein the administered compound has a formula where $R_8$ is fluorine.

17. The method of claim 14 wherein the administered compound has a formula where $R_7$ is methoxy and $R_8$ is fluorine.

18. A method of treating neuromuscular dysfunction of the lower urinary tract in a mammal in need of such treatment, comprising administering to said mammal a therapeutically effective amount of a COX-2 selective compound of the general formula III,

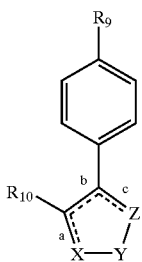

(III)

or a pharmaceutically acceptable salt thereof, wherein, when side b is a double bond and sides a and c are single bonds X-Y-Z is selected from the group consisting of
—$CH_2CH_2CH_2$—,
—$C(O)CH_2CH_2$—,
—$CH_2CH_2C(O)$—,
$CR_{11}(R'_{11})$—O—C(O)—,
—C(O)—O—$CR_{11}(R'_{11})$—,
—$CR_{11}(R'_{11})$—$NR_{12}$—C(O)—,
—N=$CR_{13}$—O—,
—O—$CR_{13}$=N—, and
—C(O)—$NR_{12}$—$CR_{11}(R'_{11})$—;
or when sides a and c are double bonds and side b is a single bond X-Y-Z is selected from the group consisting of
=CH—O—CH=,
=CH—$CR_{11}(R'_{11})$—CH=,
=CH—$NR_{12}$—CH=,
=N—O—$CR_{11}$=,
=CH—O—N=, and
=N—O—N=;

where $R_9$ represents a group of formula $NHS(O)_2CH_3$, $S(O)_2CH_3$, $S(O)_2NH_2$, $S(O)(NH)NH_2$ or $S(O)_2NHC(O)(CH_2)_{1-3}CH_3$;

$R_{10}$ represents a $C_{1-6}$-alkyl, $C_{3-7}$-cycloalkyl, or unsubstituted mono-, di- or tri-substituted phenyl or naphthyl group, wherein each potential substituent of the phenyl or naphthyl group is selected from the group consisting of halogen atom, $C_{1-6}$-alkyl, $C_{1-6}$-alkoxy, cyano and trifluoromethyl groups;

$R_{11}$ and $R'_{11}$ are each independently selected from the group consisting of hydrogen atom and $C_{1-6}$-alkyl group;

$R_{12}$ represents a hydrogen atom, trifluoromethyl, $C_{1-6}$-alkyl, hydroxy or $C_{1-6}$-alkoxy group; and $R_{13}$ represents a hydrogen atom, $C_{1-6}$-alkyl, or trifluoromethyl group.

19. The method of claim 18 wherein said mammal is a human.

20. The method of claim 18 where $R_9$ represents a $S(O)_2CH_3$, $S(O)_2NH_2$ or $S(O)_2NHC(O)CH_2CH_3$ group.

21. The method of claim 18 where $R_{10}$ represents a methyl, ethyl or unsubstituted, mono- or di-substituted phenyl group, each potential substituent of the phenyl group selected from the group consisting of halogen atom, methyl, ethyl, methoxy, ethoxy and trifluoromethyl groups.

22. The method of claim 18 where $R_{10}$ represents a phenyl group.

23. The method of claim 18 where side b is a double bond and X-Y-Z represents the group —C(O)—O—$CR_{11}(R'_{11})$—.

24. The method of claim 23 wherein the administered compound has a structure where $R_9$ is $S(O)_2CH_3$.

25. The method of claim 23 wherein the administered compound has a formula wherein $R_{10}$ represents a methyl, ethyl, or phenyl group, said phenyl group optionally substituted with 1 or 2 substituents selected from the group consisting of halogen atom, methyl, ethyl, methoxy, ethoxy, and trifluoromethyl groups.

26. The method of claim 25 wherein $R_{10}$ represents a phenyl group.

27. The method of claim 23 wherein the administered compound has a formula where $R_{11}$ and $R'_{11}$ represent hydrogen atoms.

28. The method of claim 18 where side b is a single bond and X-Y-Z represents the group =N—O—$CR_{11}$=.

29. The method of claim 28 wherein the administered compound has a formula where $R_9$ represents a $S(O)_2NH_2$ or $S(O)_2NHC(O)CH_2CH_3$ group.

30. The method of claim 28 where $R_{11}$ represents a methyl group.

31. The method of claim 28 wherein the administered compound has a formula where $R_{10}$ represents a methyl, ethyl or phenyl group, said phenyl group optionally substituted with 1 or 2 substituents selected from the group consisting of halogen atom, methyl, ethyl, methoxy, ethoxy, and trifluoromethyl groups.

32. The method of claim 31 wherein the administered compound has a formula wherein $R_{10}$ represents a phenyl group.

33. The method of claim 18 wherein Formula I represents a compound selected from the group consisting of 4-(4-methylsulfonylphenyl)-3-phenyl-2,5-dihydrofuran-2-one (Compound C);

4-(4-sulfamoylphenyl)-5-methyl-3-phenyl-isoxazole (Compound D); and

4-[4-(N-propionylsulfamoyl)-phenyl]-5-methyl-3-phenyl-isoxazole (Compound E).

34. A method of treating neuromuscular dysfunction of the lower urinary tract in a mammal in need of such treatment, comprising administering to said mammal a therapeutically effective amount of a COX-2 selective compound of the general formula V,

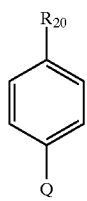

(V)

or a pharmaceutically acceptable salt thereof, wherein $R_{20}$ represents a $NHS(O)_2CH_3$, $S(O)_2CH_3$, $S(O)_2NH_2$, $S(O)(NH)NH_2$ or $S(O)_2NHC(O)(CH_2)_{1-3}CH_3$, group and Q is selected from the group of radicals consisting of

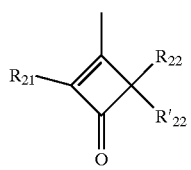

Q(i)

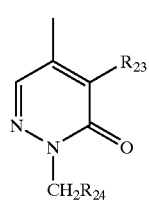

Q(ii)

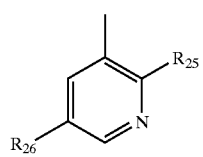

Q(iii)

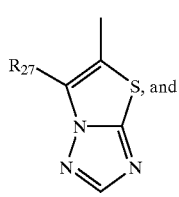

Q(iv)

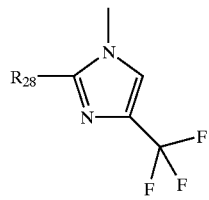

Q(v)

wherein $R_{21}$ represents a $C_{1-6}$-alkyl, $C_{3-7}$-cycloalkyl or unsubstituted, mono-, di- or tri-substituted phenyl or naphthyl group, wherein each potential substituent of the phenyl or naphthyl group is selected from the group consisting of halogen atom, $C_{1-6}$-alkyl, $C_{1-6}$-alkoxy, cyano and trifluoromethyl groups;

$R_{22}$ and $R'_{22}$ are each independently selected from the group consisting of hydrogen atom and $C_{1-6}$-alkyl group;

$R_{23}$ represents a hydrogen atom, trifluoromethyl, $C_{1-6}$-alkyl, hydroxy, or branched or unbranched $C_{1-6}$-alkoxy group;

$R_{24}$ represents a $C_{1-6}$-alkyl, $C_{3-7}$-cycloalkyl group, or unsubstituted, mono-, di- or tri-substituted phenyl group, each potential substituent of the phenyl group selected from the group consisting of halogen atom, $C_{1-6}$-alkyl group, $C_{1-6}$- alkoxy, cyano, and trifluoromethyl groups;

$R_{25}$ represents a $C_{1-6}$-alkyl, $C_{3-7}$-cycloalkyl group or unsubstituted, mono-, di- or tri-substituted aryl or heteroaryl group, wherein each potential substituent of the aryl or heteroaryl group is selected from the group consisting of halogen atom, $C_{1-6}$-alkyl, $C_{1-6}$-alkoxy, cyano, and trifluoromethyl groups;

$R_{26}$ represents a hydrogen or halogen atom, $C_{1-6}$-alkyl or $C_{1-6}$-alkoxy group;

$R_{27}$ represents a $C_{1-6}$-alkyl, $C_{3-7}$-cycloalkyl group, or unsubstituted mono-, di- or tri-substituted phenyl group, wherein each potential substituent of the phenyl group is selected from the group consisting of halogen atom, $C_{1-6}$-alkyl, $C_{1-6}$-alkoxy, cyano and trifluoromethyl groups; and $R_{28}$ represents an unsubstituted, mono-, di-, or tri-substituted heteroaryl group.

35. The method of claim 34 wherein said mammal is a human.

36. The method of claim 34 wherein the administered compound has a formula where $R_{20}$ represents a $S(O)_2CH_3$ or $S(O)_2NH_2$ group.

37. The method of claim 34 wherein the administered compound is represented by formula V in which Q represents group Q(i).

38. The method of claim 37 wherein $R_{21}$ represents an unsubstituted, mono- or di-substituted phenyl group wherein each potential substituent on the phenyl group is selected independently from the group consisting of halogen atom, methyl, ethyl, methoxy, ethoxy, or trifluoromethyl groups.

39. The method of claim 38 where $R_{21}$ represents a phenyl group, optionally substituted with 1 or 2 halogen atoms.

40. The method of claim 39 wherein $R_{21}$ represents a phenyl group.

41. The method of claim 37 wherein the administered compound has a formula where $R_{22}$ and $R'_{22}$ represent methyl groups.

42. The method of claim 41 wherein the administered compound has a formula where $R_{21}$ is phenyl and $R_{22}$ and $R'_{22}$ are each methyl.

43. The method of claim 34 wherein the administered compound is represented by formula V in which Q represents group Q(ii).

44. The method of claim 43 wherein $R_{23}$ represents a methyl, ethyl, methoxy, ethoxy, n-propoxy, or 2-propoxy group.

45. The method of claim 43 wherein $R_{24}$ represents an unsubstituted, mono-, di- or tri-substituted phenyl group, each potential substituent of said phenyl group selected from the group consisting of halogen atom, $C_{1-6}$-alkyl, $C_{1-6}$-alkoxy, cyano and trifluoromethyl groups.

46. The method of claim 45 wherein $R_{24}$ represents an unsubstituted, mono- or di-substituted phenyl group, wherein each potential substituent of the phenyl group is a halogen atom.

47. The method of claim 43 wherein $R_{23}$ is 2-propoxy and $R_{24}$ is phenyl.

48. The method of claim 34 wherein the administered compound is represented by formula V in which Q represents group Q(iii).

49. The method of claim 48 wherein $R_{25}$ represents a heteroaryl group, optionally substituted with 1–3 substituents selected independently from the group consisting of halogen atom, $C_{1-4}$-alkyl and $C_{1-4}$-alkoxy groups.

50. The method of claim 49 wherein $R_{25}$ represents a mono- or di-substituted pyridinyl group, each substituent selected independently from the group consisting of halogen atom, $C_{1-4}$-alkyl and $C_{1-4}$-alkoxy groups.

51. The method of claim 50 wherein $R_{25}$ represents a mono- or di-substituted pyridinyl, each substituent selected independently from the group consisting of halogen atom, methyl, ethyl, methoxy and ethoxy groups.

52. The method of claim 50 wherein $R_{25}$ is a pyridinyl group, optionally substituted with a $C_{1-4}$-alkyl group.

53. The method of claim 52 wherein $R_{25}$ is a 2-methyl-5-pyridyl group.

54. The method of claim 48 wherein $R_{26}$ is a halogen atom.

55. The method of claim 54 wherein $R_{26}$ is a chlorine or fluorine atom.

56. The method of claim 55 wherein $R_{26}$ is a chlorine atom.

57. The method of claim 48 wherein the administered compound is 3-(4-methylsulfonylphenyl)-2-(2-methyl-5-pyridyl)-5-chloro-pyridine.

58. The method of claim 34 wherein the administered compound is represented by formula V in which Q represents group Q(iv).

59. The method of claim 58 where $R_{27}$ represents an unsubstituted, mono-, di-or tri-substituted phenyl group, each potential substituent selected from the group consisting of halogen atom, $C_{1-6}$-alkoxy and $C_{1-6}$-alkyl groups.

60. The method of claim 59 wherein $R_{27}$ represents a phenyl group.

61. The method of claim 34 wherein the administered compound is represented by formula V in which Q represents group Q(v).

62. The method of claim 61 wherein $R_{28}$ represents a 3-pyridyl or 4-thiazolyl group, optionally substituted with a $C_{1-4}$-alkyl group.

63. The method of claim 62 where the administered compound is selected from the group of compounds consisting of 1-(4-methylsulfonylphenyl)-2-(3-pyridyl)-4-rifluoromethyl-imidazole;

1-(4-sulfamoylphenyl)-2-(2-methyl-3-pyridyl)-4-trifluoromethyl-imidazole; and 1-(4-sulfamoylphenyl)-2-(2-methyl-4-thiazolyl)-4-trifluoromethyl-imidazole.

64. A method of treating neuromuscular dysfunction of the lower urinary tract in a mammal in need of such treatment, comprising administering to said mammal a therapeutically effective amount of a COX-2 selective compound of the general formula VI,

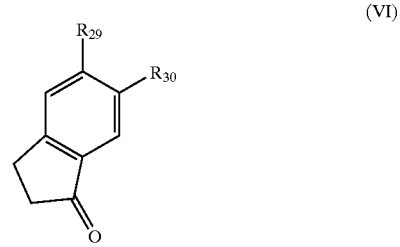

(VI)

or a pharmaceutically salt thereof, wherein $R_{29}$ represents a $NHS(O)_2CH_3$, $S(O)_2CH_3$, $S(O)_2NH_2$, $S(O)(NH)NH_2$, or $S(O)_2NHC(O)(CH_2)_{1-3}CH_3$ group; and $R_{30}$ represents a $C_{1-6}$-alkyl, $C_{3-7}$-cycloalkyl, unsubstituted, mono-, di- or tri-substituted phenyl or phenylthio group, wherein each potential substituent of the phenyl or phenylthio group is selected from the group consisting of halogen atom, $C_{1-6}$-alkyl, $C_{1-6}$-alkoxy, cyano and trifluoromethyl groups.

65. The method of claim 64 wherein said mammal is a human.

66. The method of claim 64 wherein $R_{29}$ represents a $NHS(O)_2CH_3$, $S(O)_2CH_3$ or $S(O)_2NH_2$ group.

67. The method of claim 64 wherein $R_{30}$ represents a mono-, di- or tri-substituted phenyl or phenylthio group, wherein each substituent of the phenyl or phenylthio group is selected from the group consisting of halogen atom, $C_{1-6}$-alkoxy, and $C_{1-6}$-alkyl groups.

68. The method of claim 67 wherein $R_{30}$ represents a phenylthio group, optionally substituted with 1–3 halogen atoms.

69. The method of claim 68 wherein $R_{30}$ represents a difluorophenylthio group.

70. The method of claim 69 wherein the administered compound has the structure

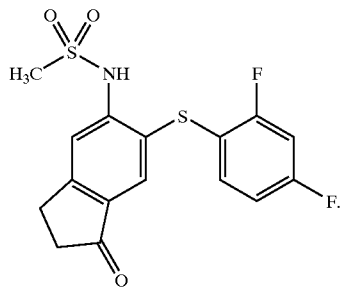

71. A method of treating neuromuscular dysfunction of the lower urinary tract in a mammal in need of such treatment, comprising administering to said mammal a therapeutically effective amount of a compound that significantly inhibits the COX-2 isozyme and which exhibits an inhibitory potency for the COX-2 isozyme that is at least about 10-fold greater than the inhibitory potency said compound exhibits for the COX-1 isozyme.

72. The method of claim 71 wherein said mammal is a human.

73. The method of claim 71 wherein the inhibitory potency of said compound is at least about 100-fold greater for the COX-2 isozyme compared to the COX-1 isozyme.

74. The method of claim 71 wherein said compound has an $IC_{50}$ of from about 0.1 to about 100 nM.

75. The method of claim 71 wherein said compound is administered via an oral, transdermal, enteral, intravenous, intramuscular, subcutaneous, transmucosal or inhalatory route.

76. The method of claim 71 wherein said compound is administered as part of a pharmaceutically acceptable composition.

77. The method of claim 71 wherein said compound is administered in a dose of about 0.05 to 50 mg/kg/day.

78. A method for identifying a compound that is a candidate for treating neuromuscular dysfunction of the lower urinary tract in a mammal comprising the steps of:
(a) measuring the inhibitory effects of said compound on COX-2 and COX-1 isozymes; and
(b) determining that a test compound that
1) inhibits the COX-2 isozyme at a concentration below about $10^{-7}$ M and
2) inhibits COX-1 isozyme with an $IC_{50}$ that is at least about 10-fold greater than the $IC_{50}$ the compound exhibits for the COX-2 isozyme is a candidate for treating neuromuscular dysfunction of the lower urinary tract.

79. The method of claim 78 wherein said mammal is a human.

80. The method of claim 78 wherein said test compound is determined to be a candidate for treating neuromuscular dysfunction of the lower urinary tract by evaluating the affect of said test compound in an animal model.

81. The method of claim 78 wherein said animal model evaluates the effect of said test compound on volume-induced rhythmic bladder voiding contractions.

82. A method of treating neuromuscular dysfunction of the lower urinary tract in a mammal in need of such treatment, comprising exposing lower urinary tract tissue of said mammal to a therapeutically effective amount of a compound that significantly inhibits the COX-2 isozyme and which exhibits an inhibitory potency for the COX-2 isozyme that is at least about 10-fold greater than the inhibitory potency said compound exhibits for the COX-1 isozyme.

83. The method of claim 82 wherein the said compound exhibits an inhibitory potency for the COX-2 isozyme that is at least about 100-fold greater than the inhibitory potency said compound exhibits for the COX-1 isozyme.

* * * * *